United States Patent
Mentzer et al.

(10) Patent No.: US 10,912,858 B2
(45) Date of Patent: Feb. 9, 2021

(54) PECTIN-CARBOXYMETHYLCELLULOSE MESOTHELIAL SEALANTS AND PROTECTANTS

(71) Applicant: The Brigham and Women's Hospital, Inc., Boston, MA (US)

(72) Inventors: Steven James Mentzer, Boston, MA (US); Cristian David Valenzuela, Fort Lee, NJ (US); Alexandra Brooke Ysasi, Providence, RI (US); Andrew Barrett Servais, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 15/967,071

(22) Filed: Apr. 30, 2018

(65) Prior Publication Data

US 2018/0311403 A1 Nov. 1, 2018

Related U.S. Application Data

(60) Provisional application No. 62/492,363, filed on May 1, 2017.

(51) Int. Cl.
*A61L 24/04* (2006.01)
*A61L 24/00* (2006.01)

(52) U.S. Cl.
CPC ........... *A61L 24/043* (2013.01); *A61L 24/001* (2013.01); *A61L 24/0015* (2013.01); *A61L 24/0042* (2013.01); *A61L 2300/414* (2013.01)

(58) Field of Classification Search
CPC .. A61L 24/043; A61L 24/001; A61L 24/0015; A61L 24/0042; A61L 2300/414
USPC .......................................................... 514/57
See application file for complete search history.

(56) References Cited

U.S. PATENT DOCUMENTS

2010/0069927 A1* 3/2010 Clark ..................... A61K 31/00
606/151

OTHER PUBLICATIONS

Munarin et al. Advances in biomedical applications of pectin gels. International Journal of Biological Macromolecules 51 (2012) 681-689 (Year: 2012).*
Bardell and Petsikas, "What keeps postpulmonary resection patients in hospital?," Can. Respir. J., 2003, 10: 86-89.
Benigni et al., "Structure—Activity Relationships for the Mutagenicity and Carcinogenicity of Simple and α-β Unsaturated Aldehydes," Environmen. Mol. Mutagen., 2003, 42: 136-143.
Bodega et al., "Pleural mesothelium lubrication after phospholipase treatment," Respir. Physiol. Neurobiol., 2014, 194:49-53.
Brennan, "Fibrin Glue," Blood Rev., 1991, 5:240-4.
Brunelli et al., "Predictors of Prolonged Air Leak After Pulmonary Lobectomy," Ann. Thorac. Surg., 2004, 77: 1205-10.
Chao et al., "BioGlue: Albumin/Glutaraldehyde Sealant in Cardiac Surgery," J. Card. Surg., 2008, 18: 500-503.
Ennker et al., "The impact of gelatin-resorcinol glue on aortic tissue: A histomorphologic evaluation," J. Vasc. Surg., 1994, 20: 34-43.
Filosso et al., "Digital versus traditional air leak evaluation after elective pulmonary resection: a prospective and comparative mono-institutional study," J Thorac Dis, 2015, 7: 1719-1724.
Fleisher et al., "Dumbbell Metastatic Cytosarcoma Phyllodes of the Heart and Lung," Ann. Thorac. Surg., 1990, 49: 309-311.
Fuller, "Reduction of intraoperative air leaks with Progel in pulmonary resection: a comprehensive review," J. Cardiothorac. Surg., 2013, 8: 90.
Hewitt et al., "BioGlue Surgical Adhesive for Thoracic Aortic Repair During Coagulopathy: Efficacy and Histopathology," Ann. Thorac. Surg., 2001, 71: 1609-1612.
Kaplan et al., "Histopathological effects of ethyl 2-cyanoacrylate tissue adhesive following surgical application: an experimental study," Eur. J. Cardiothorac. Surg, 2004, 25:167-72.
Kawai et al., "Sealing Effect of Cross-Linked Gelatin Glue in the Rat Lung Air Leak Model," Ann. Thorac. Surg., 2016, 102: 282-286.
Kim et al., "Influence of the softness of the parietal pleura on respiratory sliding mechanisms," Respir. Physiol. Neurobiol., 2011, 177:114-119.
Liang et al., "Quantifying the incidence and impact of postoperative prolonged alveolar air leak after pulmonary resection," J. Thorac. Cardiovasc. Surg., Apr. 2013, 145: 948-954.
McCarthy et al., "Permanent Mechanical Circulatory Support With an Implantable Left Ventricular Assist Device," Ann. Thorac. Surg., 1997, 63: 1458-1461.
Okabayashi et al., "Adhesions after abdominal surgery: a systematic review of the incidence, distribution and severity," Surg. Today, 2013, 44: 405-420.
Pedersen et al., "Comparative Study of Lung Sealants in a Porcine Ex Vivo Model," Ann. Thorac. Surg., 2012, 94: 234-240.
Petrella et al., "Efficacy and safety of Innoseal for air leak after pulmonary resection: a case-control study," J. Surg. Res., 2016, 206:22-6.
Pompili and Miserocchi, "Air leak after lung resection: pathophysiology and patients implications," J. Thorac. Dis., 2016, 8(Suppl 1): S46-S54.
VanTeeffelen et al., "Endothelial Glycocalyx: Sweet Shield of Blood Vessels," Trends Cardiovasc. Med., 2007, 17: 101-105.
Varela et al., "Estimating hospital costs attributable to prolonged air leak in pulmonary lobectomy," Euro. J. Cardio-Thoracic Surg., 2005, 27: 329-333.

* cited by examiner

*Primary Examiner* — Yih-Horng Shiao
(74) *Attorney, Agent, or Firm* — Fish & Richardson P.C.

(57) ABSTRACT

This disclosure relates to pectin-based polymer compositions and methods of use thereof to cover, protect, and seal injuries, e.g., surgical wounds, in a mesothelial tissue. The methods include obtaining a bioadhesive pectin-based polymer composition including a complex of high-methoxyl pectin (HMP) and carboxymethylcellulose (CMC) in a ratio from about 10 to 1 to 1 to 10 by weight; applying the composition to an injured mesothelial tissue; and applying pressure for at least one minute to enable the composition to bind to the mesothelial tissue.

9 Claims, 7 Drawing Sheets

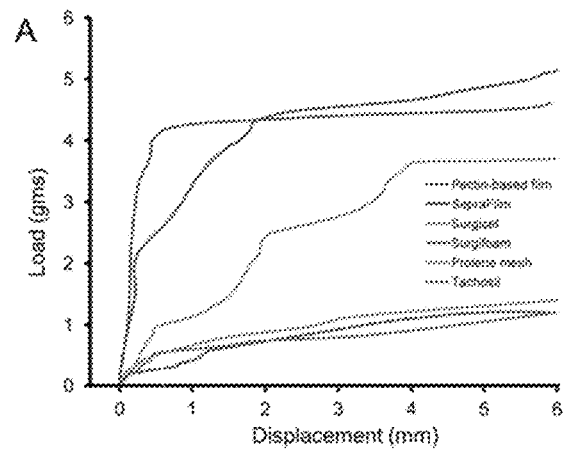
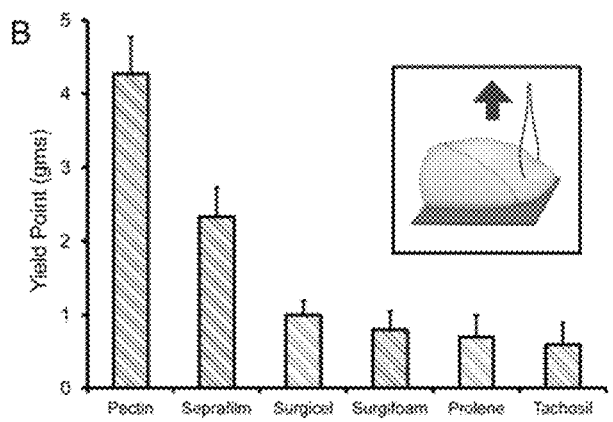
FIG. 7A  FIG. 7B
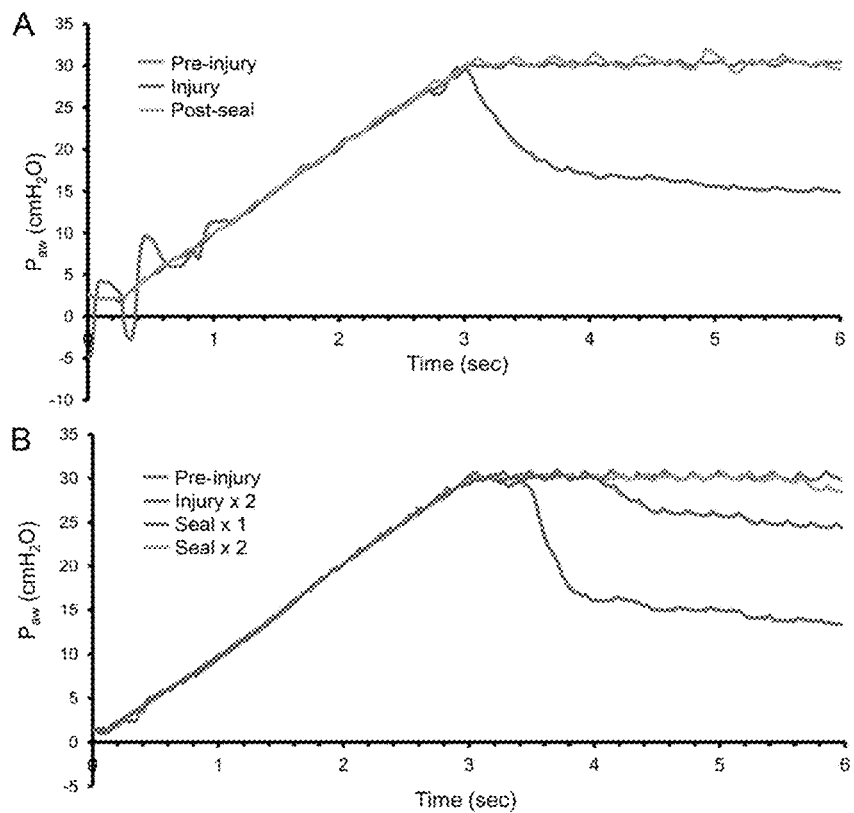
FIGs. 8A-8B

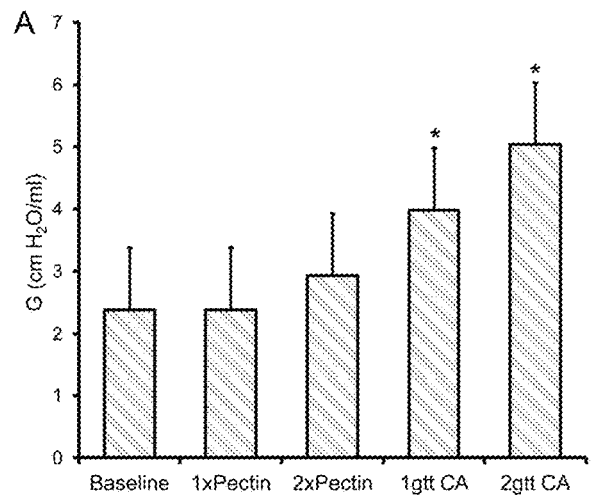
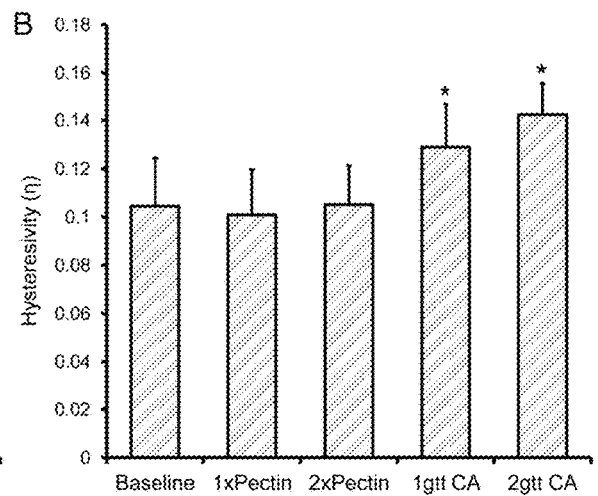
FIG. 9A  FIG. 9B
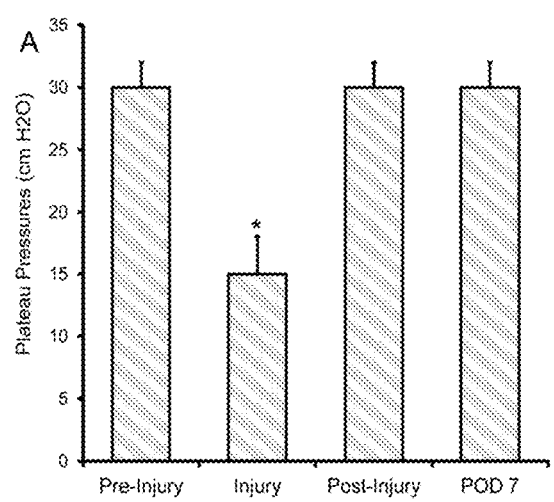
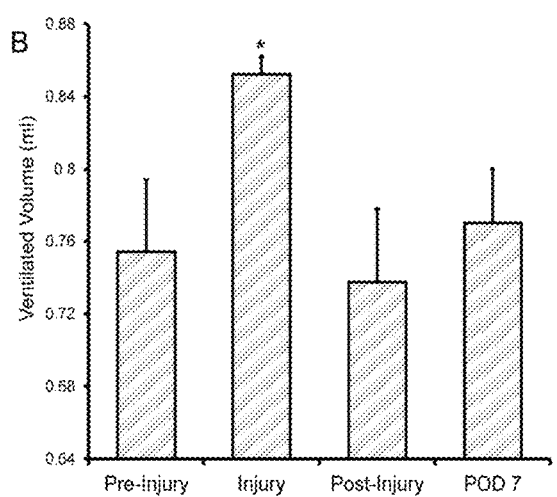
FIG. 10A  FIG. 10B

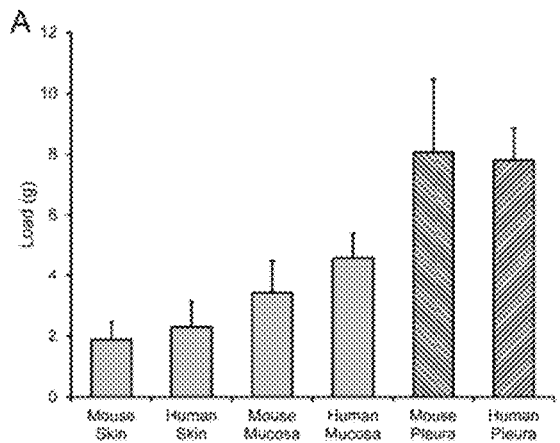
FIG. 11A
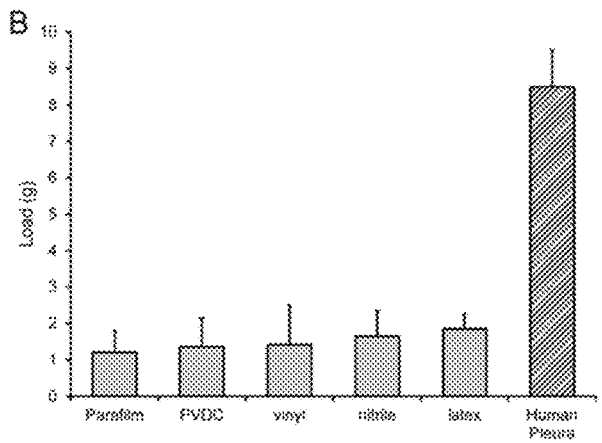
FIG. 11B
FIG. 12A
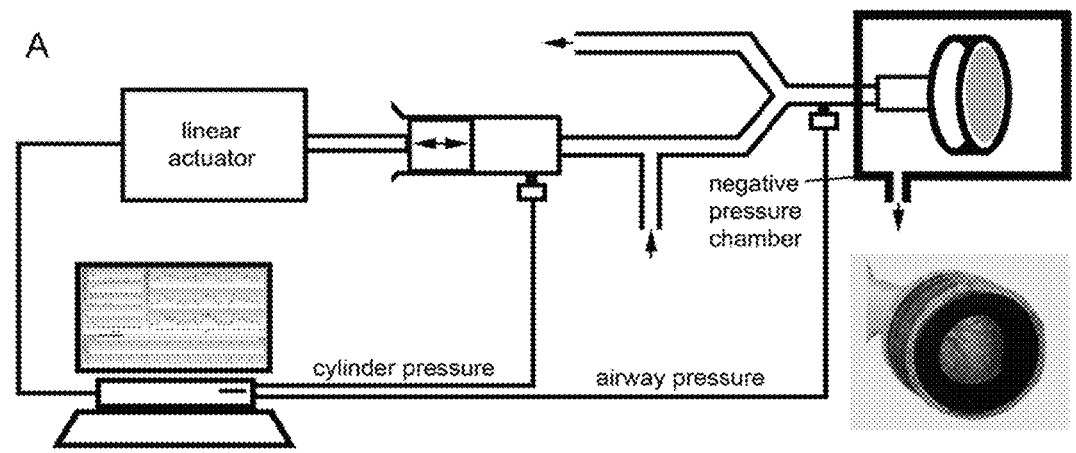
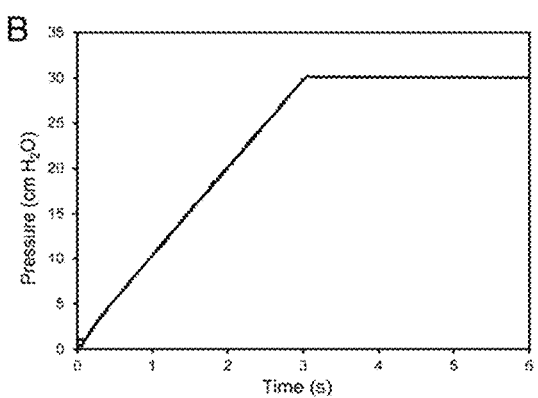
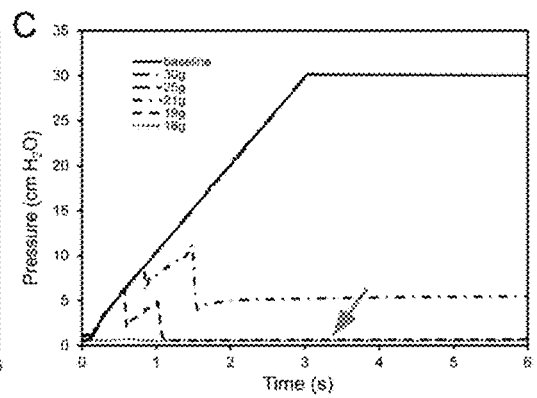
FIGs. 12B                    FIG. 12C

PECTIN-CARBOXYMETHYLCELLULOSE MESOTHELIAL SEALANTS AND PROTECTANTS

CROSS-REFERENCE TO RELATED APPLICATIONS

This application claims the benefit of U.S. Provisional Application Ser. No. 62/492,363, filed on May 1, 2017. The entire contents of the foregoing application are incorporated herein by reference.

TECHNICAL FIELD

The disclosure relates to methods and compositions for sealing and protecting mesothelial tissues.

BACKGROUND

The mesothelium is the surface barrier that separates most visceral organs from the pleural, pericardial, and peritoneal cavities. The mesothelium provides a frictionless and non-adhesive surface that facilitates the free movement of internal organs. Disruption or injury of the mesothelium creates a problem, not simply because of the compromised barrier function, but because the movement and forces associated with visceral organs (e.g., lung, bowel, and heart) can significantly compromise mesothelial healing. The slippery or non-adhesive surface of the mesothelium has compromised the use of traditional adhesives or sealants (Okabayashi et al., Surgery Today, 44:405-420, 2014).

This problem is highlighted by injury to the visceral mesothelium of the lung (pleura) causing air leaks, which not only result in air rushing out of the lung (potentially life-threatening pneumothorax), but the movement of the pleura with tidal ventilation complicates both endogenous and exogenous attempts to seal the disruption. In addition, perturbed healing results in pleural adhesions that compromise the sliding movements of the pleura (Kim et al., Respir. Physiol. Neurobiol., 177:114-119, 2011). Typically, air leaks are the result of lung surgery or trauma (Pompili and Miserocchi, J. Thorac. Dis., 8:S46-S54, 2016) and air leaks are the most common reason for increased hospital length of stay (LOS) after pulmonary surgery (Bardell and Petsikas, Can. Respir. J., 10:86-9 (2003); and Irshad et al., Can. J. Surg., 45:264-8, 2002). The impact of air leaks on patient recovery and hospital resources is significant; pleural air leaks increase LOS by five to 13 days; more than doubling of the cost of hospitalization (Varela et al., Eur. J. Cardio-Thorac. Surg., 27:329-33 (2005)). Moreover, air leaks after pulmonary surgery can lead to atelectasis, pneumonia, or empyema (Brunelli et al., Ann. Thorac. Surg., 77:1205-10, 2004). Because of these complications, post-surgical prolonged air leaks increase the rate of readmission within 30 days by 20.4% (Liang et al., J. Thorac. Cardiovasc. Surg., 145:948-54, 2013).

Attempts to treat pleural injuries have also been mostly ineffective. Previous approaches have used bioadhesive sealants and chemical cross-linkers to seal pleural air leaks. Bioadhesive sealants based on fibrin (Evicel, Ethicon, Somerville, N.J., USA) (Pedersen et al., Ann. Thorac. Surg., 94:234-40, 2012) or albumin and polyethylene glycol (Progel, Bard-Davol, Warwick, R.I., USA) (Fuller, J. Cardiothorac. Surg., 8, 2013) have the advantage of being fast-setting, biocompatible, and biodegradable. However, because of their dependence upon antigenic proteins, their use has been associated with allergic reactions (Brennan, Blood Rev., 5:240-4, 1991). In addition, poor adhesivity to the pleural surface has limited their effectiveness (McCarthy et al., Ann. Thorac. Surg., 45:203-5, 1988; Fleisher et al., Ann. Thorac. Surg., 49:133-4, 1990; and Kawai et al., Ann. Thorac. Surg., 102:282-6, 2016).

Chemical cross-linking of tissue surfaces has been attempted using albumin-glutaraldehyde adhesive (BioGlue, CryoLife, Kennesaw, Ga., USA) (Ennker et al., J. Vasc. Surg., 20:34-43, 1994; Hewitt et al., Ann. Thorac. Surg., 71:1609-12, 2001; and Chao et al., J. Cardiac Surg., 18:500-3, 2003) or cyanoacrylate derivatives (Histoacryl, Braun, Woburn, Mass., USA) (Kaplan et al., Eur. J. Cardiothorac. Surg., 25:167-72, 2004; and Petrella et al., J. Surg. Res., 206:22-6, 2016). These chemicals are fast-setting with effective adhesive strength, but their use has been limited by the risk of local toxicity and long-term carcinogenicity (Benigni et al., Environ. Mol. Mutagen., 42:136-43, 2003).

Thus, there exists a need for bioadhesives that not only can seal mesothelial tissue injuries including pleural injuries, but also prevent undesired adhesion between tissues or between tissues and organs.

SUMMARY

The present disclosure relates to pectin-based polymer compositions that can be used as bioadhesives for mesothelial tissues. The compositions include high-methoxyl pectin (HMP) and carboxymethylcellulose (CMC), in various ratios, e.g., a ratio ranging from 1 to 10 to 10 to 1, e.g., 1:9, 1:8, 1:7, 1:6, 1:5, 1:4, 1:3, 1:2, 1:1, 2:1, 3:1, 4:1, 5:1, 6:1, 7:1, 8:1, or 9:1 by weight, of HMP and CMC, cured, e.g., at room temperature. The resulting compositions can be formed as a thin moldable film having a thickness of about 40 microns to 3 mm, e.g., 50, 60, 70, 80, 90, 100, 110, 120, 130, 140, 150, 160, 170, 180, 190, or 200 microns, or 250, 300, 450, 500, 600, 700, 800, 900 microns, or 1, 1.25, 1.5, 1.75, 2.0, 2.25, 2.5, 2.75, or 3.0 mm, or can have other shapes. When applied to mesothelial tissue the film forms a strong adhesive interaction.

In another aspect, the disclosure relates to the use of the new polymer compositions, e.g., in the form of films, in methods of protecting, covering, and sealing injuries to mesothelial tissues including the pleural lining of the lungs, the pericardial lining of the heart, and the peritoneal lining of the bowel, spleen, and liver. Without being bound to a theory, the strong bioadhesive interaction that provides the protective and sealing effect appears to be the results of entanglement of the branches of the heteropolysaccharides of the mesothelial glycocalyx and of the pectin. In addition, it appears that glycocalyx in different tissues within humans and even between different species are very similar, if not indistinguishable, making the current polymers a "universal" bioadhesive for all mesothelial tissues.

In general, the disclosure features methods of covering and sealing a wound or injury in a mesothelial tissue. The methods include obtaining a bioadhesive pectin-based polymer composition including a complex of high-methoxyl pectin (HMP) and carboxymethylcellulose (CMC) in a ratio from about 10 to 1 to 1 to 10 by weight (of the composition), or a composition including 50 percent to 100 percent HMP by weight (of the composition); applying the composition to an injured mesothelial tissue; and applying pressure for at least one minute to enable the composition to bind to the mesothelial tissue.

In certain embodiments, the mesothelial tissue is lung pleura and the method is used to seal an air leak in the lungs. In other embodiments, the mesothelial tissue is heart mesothelium and the method is used to cover a wound in the heart. In other embodiments, the mesothelial tissue is bowel mesothelium, and the method is used to seal a surgical site in the bowel. In yet another embodiment, the mesothelial tissue is spleen mesothelium and the method is used to repair a ruptured spleen.

In various embodiments, the bioadhesive pectin-based polymer composition includes a 1:1 ratio by weight of HMP and CMC.

In another embodiment, the bioadhesive pectin-based polymer composition forms a moldable film having a thickness of about 40 to 3000 microns. The film can further include a second, anti-adhesive film fixed to the moldable film. In some embodiments, the bioadhesive pectin-based polymer composition biodegrades within about seven days.

In another general aspect, the disclosure includes bioadhesive, pectin-based polymer compositions that include a complex of high-methoxyl pectin (HMP) and carboxymethylcellulose (CMC) in a ratio of 10 to 1 to 1 to 10, wherein the composition binds to mesothelial tissue.

In certain embodiments, the bioadhesive composition is in the form of a moldable film having a thickness of about 40 microns to 3000 mm. In some embodiments, the bioadhesive composition further includes a second, anti-adhesion film fixed to the moldable film, wherein the second film has reduced or no bioadhesion compared to the moldable film. In certain embodiments, the bioadhesive composition further includes a second film fixed to the moldable film, wherein the second film includes less than 15% of pectin for reduced bioadhesion.

In some embodiments, the bioadhesive composition can further include one or more active agents. For example, the one or more active agents can include one or more growth factors, e.g., one or more of transforming growth factor alpha (TGF-a) and TGF-β, tumor necrosis factor-alpha (TNF-α), vascular endothelial growth factor (VEGF), leukemia inhibitory factor (LIF), interleukins such as IL-1 through IL-7, colony-stimulating factors such as macrophage colony-stimulating factor (m-CSF), granulocyte colony-stimulating factor (G-CSF), and granulocyte macrophage colony-stimulating factor (GM-CSF), fibroblast growth factor (FGF), epidermal growth factor (EGF), insulin-like growth factor, connective tissue growth factor (CTGF), hepatocyte growth factor (HGF), Angiopoietin-1-4, and platelet-derived growth factor (PDGF).

In some embodiments, the one or more active agents can include one or more of heparin, tissue plasminogen activator (tPA), aspirin, ibuprofen, ketoprofen, non-steroidal anti-inflammatory drugs, hormones, cytokines, osteogenic factors, chemotactic factors, proteins and peptides that contain an arginine-glycine-aspartate ("RGD") motif, analgesics, anesthetics, norepinephrine, epinephrine, phenylpropanolamine, dopamine, metaraminol, methoxamine, ephedrine, propylhexedrine, fibrillar collagen, thrombin, fibrin, a chemotherapy agent, and an immunotherapy agent.

The new polymer compositions provide various benefits and advantages including: (1) they form non-destructive yet secure bioadhesive interactions with mesothelial surfaces of multiple tissue types; (2) they are non-toxic and non-destructive; (3) they are able to trap substances such as growth factors, drugs, or other molecules within the pectin-based biopolymer (calcium ions cause the pectin-based biopolymer to form an egg-carton like structure that can trap various substances; and (4) they can prevent or minimize adhesions (scar tissue) after surgery or other trauma to the mesothelial tissue.

As used herein, the term "adhesion" means an abnormal attachment between two tissues or between a tissue and an organ that form after an inflammatory stimulus such as surgical or other trauma.

As used herein, the terms "adhesion inhibition" and "anti-adhesion" refer to reducing the formation of post-surgical adhesions, e.g., in the form of a scar and/or a fibrous band, between traumatized tissues, and between traumatized and non-traumatized tissues.

As used herein, the term "bioadhesive" refers to a composition that can securely bind to living tissue.

As used herein, the term "bioresorbable" when referring to a composition means that the composition can be reabsorbed and eliminated from the body.

As used herein, the term "biocompatible" means a composition that is physiologically acceptable to a living tissue and organism.

As used herein, the term "carboxymethylcellulose" (CMC) refers to a polymer composed of repeating carboxylated cellobiose units and two anhydroglucose units of β-glucopyranose residues, joined by 1,4 glucosidic linkages, wherein the cellobiose units are variably carboxylated.

As used herein, the terms "mesothelium" and "mesothelial tissue" refer to a membrane that forms the lining of several body cavities including the pleural, pericardial, and peritoneal cavities.

As used herein, the term "peritoneum" refers to the serous membrane lining the abdominal cavity and surrounding the viscera.

As used herein, a "pectin" is any one of a family of galacturonic acid-rich polysaccharides including homogalacturonan, rhamnogalacturonan I, and the substituted galacturonans rhamnogalacturonan II (RG-II) and xylogalacturonan (XGA), as described in Mohnen, "Pectin Structure and Biosynthesis," Current Opinions in Plant Biology, 11:266-277, 2008. High methoxyl pectins and amidated pectins are variations of the pectin family. As used herein, the terms "high-methoxyl pectin," "high-methyl pectin," and high methyl ester-pectin" are used interchangeably.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 3A to 3C show the adhesion strength of CMC and different weight ratios of high-methoxyl pectin (HMP), amidated low-methoxyl (LMA), and non-amidated low-methoxyl (LMC) pectin; liver adhesion is shown. The area of the bubble reflects relative adhesion strength of the different mixtures scaled to 100. The greatest adhesion strength was demonstrated in equal weight (%) ratio of all 3 pectins and CMC. FIG. 3D shows the comparison of adhesion strength of HMP, LMA, and LMC and equal weight (%) ratio mixtures of CMC tested against all four mesothelial tissues. HMP demonstrated consistently greater adhesion than comparable LMA and LMC pectin (p<0.01). FIG. 3E shows the comparison of equal weight ratio of HMP and CMC (50%) and CMC with no pectin (0%) for all four mesothelial tissues. The 50% mixture was significantly greater than the 0% mixture for all 4 tissues (p<0.01) (error bars=1 S.D. of triplicate samples).

FIG. 5A shows Scanning Electron Microscopy results of a mesothelial layer showing the typical "flagstone" appearance of the free surface of the mesothelium (ellipse) and alveolar remnants on the deep surface of the layer (arrow). FIG. 5B shows fluorescent nuclear staining, which demonstrates an intact monolayer. FIG. 5C shows silver staining, which demonstrates intact tight junctions.

FIGS. 7A and 7B are graphs showing load/displacement measurements. The adhesion of lung pleura to different surgical products was measured by a load/displacement assay (as shown in the inset of FIG. 7B). 90-degree loads were applied at a controlled rate to a suture passed through the tissue near the adhesive interface. Displacement was a measure of the separation at the adherend-substratum interface. FIG. 7A shows the representative load/displacement curves for the pectin-based bipolymer and five commercially available surgical products. The curves were highly reproducible at displacement distances less than 3 mm; greater variability was noted between 3 mm and 6 mm (representative estimates shown). FIG. 7B shows that replicates of the initial separation load (yield point) demonstrated significantly greater bioadhesion of the pectin-based polymer than the surgical products (p<0.001; N=5).

FIGS. 8A and 8B are a pair of graphs that show representative respiratory system mechanics after pleural injury. After standardizing volume history, a recruitment maneuver was performed consisting of a 3-second ramp to a 30 cm $H_2O$ airway pressure followed by a 3-second plateau. FIG. 8A shows that after a single 25 g needle-induced pleural injury, the recruitment maneuver demonstrated a plateau pressure of approximately 15 cm $H_2O$. After sealing the injury with the pectin-based polymer, the repeat recruitment maneuver restored the 30 cm $H_2O$ airway pressures. FIG. 8B shows that after a through-and-through injury of the lung, the pressures similarly dropped to less than half of the 30 cm $H_2O$ plateau pressures (Injury×2). Sealing one of the injuries with the pectin-based polymer increased plateau pressures (Seal×1). Sealing both the first and the second injury (Seal× 2) resulted in restoration of baseline airway pressures. Note the two phases of the pressure curve: the initial exponential decline in airway pressures followed by a quasi-plateau phase. Most commercial sealants fail because they do not stick to the lung, or they cannot accommodate to the change in lung volume with ventilation. These data show that the pectin adhesive accommodates the stretch in the lung, which is a distinctly unique feature. Summary data of a single pleural injury is shown in FIGS. 10A and 10B.

FIGS. 9A and 9B are a pair of bar graphs that show the effects of sealants on peripheral lung mechanics. Lung impedance measurements were made using a forced oscillation technique (FlexiVent®). The no sealant condition (Baseline) was compared to two sizes of the pectin-based polymer (1×Pectin, 25 $mm^2$; 2×Pectin, 50 $mm^2$) as well as two volumes of a cyanoacrylate (CA, VetBond®) sealant (1 gtt, 25 μl; 2 gtt, 50 μl). FIG. 9A shows the measurement of tissue damping (G) demonstrated a slight increase in the 2×Pectin condition (p>0.05), but a significant increase in both cyanoacrylate conditions (asterisk, p<0.01). FIG. 9B shows hysteresivity, reflecting the relationship between energy dissipation and energy conservation (elastance), demonstrated no difference in the pectin-based polymer conditions, but a significant increase in the cyanoacrylate treatment groups (asterisk, p<0.01). Triplicate measures per mouse; each data point represents N=3 mice.

FIGS. 10A and 10B are a pair of bar graphs that show respiratory system mechanics seven days after application of the pectin-based polymer. FIG. 10A shows that acutely after injury with a 25 g needle, significantly decreased plateau pressures (asterisk, p<0.001) were restored after application of the pectin-based polymer. The plateau pressures remained at baseline levels after 7 days. FIG. 10B shows that similarly, the significant increase in ventilated volume ("leak volume") after pleural injury (asterisk, p<0.001) was normalized after application of the pectin-based sealant. The ventilatory efficiency remained unchanged after 7 days. Triplicate measures per mouse; each data point represents N=5 mice.

FIG. 11A is a bar graph that shows that in biologic testing the pectin-based polymer demonstrated progressive adhesion strength in binding to human and mouse skin, mouse and human buccal mucosa, and mouse and human pleura (N=5). Binding strength of the polymer to the pleura was greater than the binding to skin or mucosa (p<0.01). There was no statistical difference between human and mouse pleura.

FIG. 11B is a bar graph that shows that in non-biologic testing, the pectin-based polymer demonstrated minimal binding to the moist interface of the adherend (parafilm, PVDC, vinyl, nitrile, and latex; dry surfaces demonstrated no detectable binding. Human pleural bioadhesion is shown for comparison and is significantly greater (p<0.0001). Quintuplicate samples are shown; error bars are ±1 std. dev.

FIG. 12A is a schematic diagram of a simulacrum used for pressure-decay leak testing of human pleura. A FlexiVent® ventilator (SciReq, Montreal, Calif.) was used to monitor pressures during the computer-controlled 3 second ramp to 30 cm $H_2O$ followed by a 3 second pressure plateau. In testing biologic samples, the human pleural sample (shown in gray inset) was placed in a negative pressure chamber with a range of 0 to −40 cm $H_2O$ to extend the transpleural pressure range of the system.

FIGS. 12B and 12C are graphs that show the results of testing in the simulacrum represented in FIG. 12A. FIG. 12B shows baseline testing of pleural samples, in which the inflation maneuver resulted in a stable pressure plateau. FIG. 12C shows that under the test conditions, the mounted pleura was perforated by a needle of various caliber: 30 g, 25 g, 21 g, 19 g, and 16 g. Representative pressure decays are shown. In most cases, perforation of a 21 g or 19 g needle resulted in inflation failure (arrow). All pleural samples demonstrated lower pressure-decay curves with increasing needle caliber. Because of the variable thickness of the pleural tissue, complete decompression was empirically obtained prior to application of the pectin-based sealant.

FIGS. 13A-D show results when perforated human pleural tissue was sealed with four different pectin mixtures. Solid lines show baseline inflation maneuver to 30 cm $H_2O$; dotted lines reflect the pressure curves of four representative samples. The gray shading reflects the transpleural pressure level (ventilator pressure+negative pressure chamber): FIG. 13A −10 cm $H_2O$, 13B −10 cm $H_2O$, 13C −20 cm $H_2O$, and 13D −30 cm $H_2O$.

FIG. 13E is a bar graph that shows the mean peak transpleural pressures prior to sealant failure based on N=5 samples, and the results demonstrated a significant difference between HMP and CMC and LMA (p<0.001) and an improvement over LMC. Error bars reflect ±1 std. dev.

FIG. 13F is a graph that shows similar data presented as a product-limit estimator shows the superior sealant performance of the 50% HMP:CMC mixture vs. 100% CMC, 50% LMA, 50% LMC, and 100% HMP; N=12 samples, p<0.01.

DETAILED DESCRIPTION

Figures 1A, 1B, 1C:
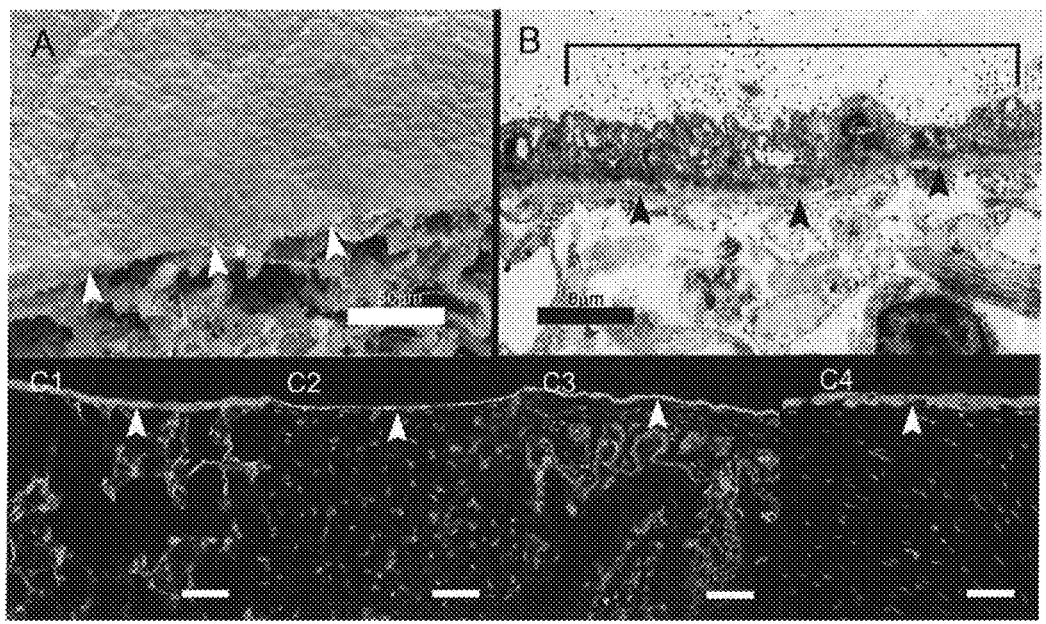
FIG. 1A is a Scanning Electron Micrograph of the murine lung visceral pleura. The "flagstone" appearance of the mesothelium was demonstrated above the cut surface of the lung (arrows).
FIG. 1B is a Transmission Electron Micrograph (TEM) of the visceral pleural mesothelium demonstrated microvilli (bracket) and the underlying mesothelial basement membrane (black arrows). The intervillar glycocalyx was not seen in TEM.
FIG. 1C is a micrograph showing staining of visceral mesothelium with the green fluorescent lectin *Lycopersicon esculentum* (LEL) (Vector Laboratories) demonstrated the glycocalyx (arrows) in the lung (C1), liver (C2), bowel (C3), and heart (C4). The blue nuclei reflected Hoechst 33342 (Sigma) counterstain (Bars=60 μm).

New pectin-based polymer compositions that can be used as a bioadhesive for mesothelial tissues include a mixture of high-methoxyl pectin (HMP) and carboxymethylcellulose (CMC) that is cured, e.g., air-dried, for a sufficient time and under conditions, e.g., at room temperature, to form a thin, moldable film or other shapes. When exposed to mesothelial tissue the new compositions form a strong adhesive interaction. In some embodiments, the bioadhesive interaction can be controlled, e.g., reduced or reversed, with a change in hydration or the use of enzymes such as glycosidases and glycoside hydrolases during application of the pectin-based compositions to the mesothelial tissues.

In addition to binding mesothelial tissues together, the bioadhesive properties of the new polymer compositions, e.g., films, can be used to seal air leaks in the lungs. The strong binding properties are consistent across multiple types of mesothelial tissue including the pleural lining of the lungs, the pericardial lining of the heart, and the peritoneal lining of the bowel, spleen, and liver.

Pectin-Based Compositions

The new pectin-based compositions include pectin, e.g., HMP, and CMC in a ratio ranging from 1 to 10 to 10 to 1, e.g., 1 to 7, 1 to 5, 1 to 4, 1 to 3, 1 to 2, 1 to 1, 2 to 1, 3 to 1, 4 to 1, 5 to 1, 7 to 1, or 9 to 1. In some embodiments, 100% pectin can be used.

Pectins are a family of plant cell wall polysaccharides and/or glycan domains that consist mainly of esterified D-galacturonic acid residues in (1→4) chains (Monsoor et al., Food Chem., 74:233-8 (2001); Nunes et al., Carbohydr. Polym., 87:620-6 (2012)). Pectins differ from typical pressure sensitive adhesives, as they do not bind to most non-biologic compounds. However, they selectively and strongly bind to the mesothelial glycocalyx (Servais et al., Tissue Eng. Part A, 24:199-206, 2018), which is likely the result of a mechanism of interdiffusion or interpenetration (Leung et al., J. Control. Release., 12:187-94, 1990), e.g., the entanglement of branched chain polysaccharides (Mehdizadeh et al., Macromol. Biosci., 13:271-88, 2013) based on chemical bonds and weak chemical interactions (Sriamornsak et al., Carbohydr. Polym., 74:458-67 (2008); Boateng et al., Curr. Pharm. Des., 21:4798-821 (2015), and Mansuri et al., React. Funct. Polym., 100:151-72, 2016).

Pectins can vary in molecular weight, cross-linking density (determined by multi-angle laser light scattering) (Chen et al., 2014), and chemical groups (e.g., hydroxyl, amine, sulfur and carboxyl groups) (Duchene et al., 1988; Robert et al., 1988; Leung and Robinson, 1990). The polysaccharides that make up pectin are generally grouped into three major types: homogalacturonan (HG), rhamnogalacturonan I (RG-I), and the substituted galacturonanrhamnogalacturonan II (RG-II). Some plant cell walls also contain additional substituted galacturonans, known as apiogalacturonan (AGA)

and xylogalacturonan (XGA). Thus, pectins are often defined by their source, e.g., citrus pectin (which is used in the examples described herein). The most common categories of pectin vary with respect to amidation and methoxylation; however, all pectins appear to be biocompatible. When exposed to calcium, pectin forms egg box-like structures that facilitate the immobilization of substances within the gel structure (Munarin et al., Biomacromolecules, 12:568-77 (2011).

The pectins used to prepare the new polymer compositions described herein are preferably high-methoxyl pectins (HMP), which can be obtained commercially (e.g., from Cargill, Minneapolis, Minn., USA). The proportion of galacturonic acid residues in the methyl ester form determines the degree of methoxylation. HMPs are defined herein as those pectins with a degree of methoxylation greater than 50%; low-methoxyl pectins (LMP) are defined herein as those pectins with a degree of methoxylation of less than 50%. The LMP were also tested as non-amidated (LMC) and amidated (LMA) variants. While there are several different methods of determining the degree of methoxylation of pectin, the quantitative test used herein to determine the degree of methoxylation of a given pectin is an NMR-bsed method described in Mueller-Maatsch et al., J. Agric. Food Chem., 62:9081-9087 (2014).

Methods of Making Compositions and Films

To prepare the new polymer compositions, the pectins are mixed with carboxymethylcellulose (CMC), also known as cellulose gum or tylose powder is a cellulose derivative with carboxymethyl groups (—$CH_2$—COOH) bound to some of the hydroxyl groups of the glucopyranose monomers that make up the cellulose backbone. CMC is often used as its sodium salt, sodium carboxymethyl cellulose. CMC is synthesized by an alkali-catalyzed reaction of cellulose with chloroacetic acid. The polar carboxyl groups render the cellulose soluble and chemically reactive.

Following the initial reaction, the resultant mixture produces about 60% CMC plus 40% salts (sodium chloride and sodium glycolate). A further purification process is used to remove these salts to produce pure CMC, which can be used for food, pharmaceutical, and other applications. The properties of CMC depend on the number of hydroxyl groups, the chain length of the cellulose backbone structure, and the degree of clustering of the carboxymethyl substituents.

The liquid compositions can be prepared and cast onto a surface or into a mold to create a thin, moldable film, or poured into a mold to create various shaped implants, e.g., to fill a specific wound, surgical excision, or trauma in the tissue, and then cured for a sufficient time to harden, e.g., 1, 2, 3, 4, 5, 6, 7, 8, 9, 10, 11, 12, 13, 14, 15, 17, 20, 24 or more hours, e.g., under conditions that promote curing, e.g., a temperature of 20-25° C. or warmer. The thin films or sheets can be about 40 to 3000 microns (in general, the thicker the film, the longer the curing time).

The pectin-based compositions described herein are not intended to stay in the body indefinitely, but instead are designed to biodegrade within a specific length of time. Once placed at a surgical or injury site and healing has taken place, the bioadhesive pectin-based compositions naturally disintegrate, and the components are cleared from the body. The time taken to clear the body for certain embodiments is desirable no more than 29 days because of increased regulation by the Food and Drug Administration of devices intended to remain within the body for more than 30 days. However, it may be useful in some embodiments to provide longer-duration compositions.

By changing the solubility properties, the pectin-based polymer compositions can be designed for different residence times in the body once implanted. To achieve these different residence times in the body, one can vary percentages and branch chain-lengths of the HG, RG-I, and RG-II polysaccharides to vary the solubility properties of the pectin-base polymer compositions. In addition, the degree of methylation can be altered to control the solubility and residence time of the pectin-based compositions once implanted in the body. In general, a lower degree of methylation for the pectin provides faster biodegradation and thus a shorter residence time once implanted.

One-Sided Pectin-Based Polymer Films

In some embodiments, the pectin-based polymer composition films can be composed of two or more layers, with differing ratios of components in each layer. The result is a film that is more bioadhesive on one side than the other, which is an important feature when using the films to avoid tissue adhesions, e.g., post-surgical tissue adhesions, for example post-surgical pleural/serosal adhesions. These films have at least two layers, e.g., have multiple layers, in which one side, the bioadhesive side, includes at least 50% pectin, e.g., 60, 70, 80, 90, or 100% pectin, and the non-bioadhesive (or reduce bioadhesive) side includes less than 15% pectin, e.g., 12, 10, 7, 5, 4, 3, 2, 1, or 0% pectin, and greater than 15% CMC or other non-bioadhesive, biodegradable cellulose-related polymer and/or silicone. In some embodiments, the non-bioadhesive side may include a non-biodegradable, but biologically inert, material.

The application of this technology to prevent adhesions can significantly reduce morbidity and healthcare costs in both the chest and abdomen—particularly, those costs associated with post-surgical bowel obstruction. Thus, the disclosure includes methods of reducing or inhibiting post-surgical bowel obstruction by applying a pectin-based composition film that includes a pectin-based bioadhesive side and a non- or reduced-adhesion side.

Pectin-Based Polymers as Drug Delivery Systems

In some embodiments, one or more active agents can be incorporated into the pectin-based polymer either during manufacture or after the polymer has been made and before or after application to a mesothelial tissue. Because of pectin's "egg-box" structure when exposed to calcium ions, drugs, wound healing agents, and/or growth factors can be readily incorporated into the polymer to accelerate healing and/or limit adhesions. In particular, the new polymers can include active agents that are water soluble, in the form of nanoparticles, and/or are lipophilic.

In general, any drug or other active agent that is compatible with the polymer compositions and methods of manufacture can be used with the present compositions and methods. Useful active agents include growth factors such as transforming growth factors, e.g., transforming growth factor alpha (TGF-α) and TGF-β, tumor necrosis factor-alpha (TNF-α), vascular endothelial growth factor (VEGF), leukemia inhibitory factor (LIF), interleukins such as IL-1 through IL-7, colony-stimulating factors such as macrophage colony-stimulating factor (m-CSF), granulocyte colony-stimulating factor (G-CSF), and granulocyte macrophage colony-stimulating factor (GM-C SF), fibroblast growth factor (FGF) (e.g., FGFs 1 through 23), epidermal growth factor (EGF), insulin-like growth factor (e.g., IGF-1 and IGF-2), connective tissue growth factor (CTGF), hepatocyte growth factor (HGF), Angiopoietin-1-4, and platelet-derived growth factor (PDGF).

Other useful active agents may inhibit adhesion formation such as anti-thrombogenic agents, e.g., heparin or tissue plasminogen activator (tPA), and anti-inflammatory agents, such as aspirin, ibuprofen, ketoprofen, or other, non-steroidal anti-inflammatory drugs. Furthermore, hormones, cytokines, osteogenic factors, chemotactic factors, proteins and peptides that contain an arginine-glycine-aspartate ("RGD") motif, analgesics, or anesthetics can be added to the polymer compositions. Other useful active agents include vasoconstrictors such as adrenergic agonists, e.g., norepinephrine, epinephrine, phenylpropanolamine, dopamine, metaraminol, methoxamine, ephedrine, and propylhexedrine, fibrillar collagen, and clotting factors such as thrombin and fibrin. In addition, in some embodiments, the one or more active agents can be chemotherapeutic agents (such as one or a combination of pemetrexed (Alimta®), cisplatin, carboplatin, gemcitabine, doxorubicin, onconase, methotrexate, vincristine, vinblastine, mitomycin, vinorelbine, epirubicin, cyclophosphamide, and ifosfamide) and immunotherapeutic agents (such as anti-semaphorin 4D (SEMA4D), ipilimumab (anti-CTLA-4), anti-PD-1/PD-L1 agents, intratumoral toll-like receptor nine (TLR9) agonists, selective MEK1 and MEK2 inhibitors such as cobimetinib, CDX-1401, CDX-301, and varlilumab).

Methods of Sealing and Protecting Mesothelial Tissues

Although the mechanism of bioadhesion is poorly understood, the first step in the process of bioadhesion to, or sealing of, a mesothelial tissue injury is to provide intimate contact between the pectin-based polymer compositions and the mesothelial tissue for at least about 1, 2, or 3 minutes with slight pressure. This phase increases the contact area between the surfaces. The second phase involves the interpenetration of the branches of the heteropolysaccharides of the mesothelial glycocalyx and of the pectin. The interpenetrated chains interact, forming entanglements as well as chemical bonds and weak chemical interactions.

As described in the examples below, the new methods have been demonstrated to work with the surface glycocalyx of the lung, liver, bowel, and heart mesothelium, but the new methods can be used with all types of mesothelium in humans and animals. Mesothelium is the surface layer to serosal tissues of the pleura, pericardium, peritoneum, and tunica vaginalis. The mesothelium is covered by a glycocalyx that functions to limit fluid loss (VanTeeffelen et al., Trends Cardiovasc. Med., 17: 101-5, 2007) and minimize frictional forces (Bodega et al., Respir. Physiol. Neurobiol., 194:49-53, 2014). The adhesive strength of pectin to the mesothelial glycocalyx was sufficient to not only establish selective interfacial adhesion, but also permit the intact isolation of visceral pleural mesothelium.

Air-leaks are a common problem in thoracic surgery. They are caused by holes in the pleura or lung that allow air to escape from the airways into the surrounding pleural space causing collapse of the lung itself. Often in the post-operative period, air may leak via staple-lines of previously resected lung tissue or through other points of iatrogenic injury. Post-operative thoracic surgery patients with air leaks require a chest tube that cannot be removed until the air leak resolves. If the air leaks do not resolve spontaneously, they require re-operation.

The new pectin-based polymer compositions form a hydrogel with strong bioadhesion to the mesothelial tissue of the lung. The examples below demonstrate that this bioadhesive property can be utilized to create a strong adhesive "patch" to seal holes in the lung tissue and stop air leaks. Thus, the pectin-based polymers can be used intraoperatively to cover and seal damaged areas of the lung that leak air.

The low-cost sealants are safe and nontoxic. Constituted as a 50 µm thick film, the pectin-based sealant compositions are easily prepared and readily applied to the injured pleura—requiring only a 1-2 minutes of gentle pressure to seal the air leak. Clinical and histologic evidence shows that the sealant persists throughout a typical seven-day healing process, but the compositions can be designed to provide a shorter or longer period of persistence in the body, e.g., 3, 5, 7, 9, 10, 12, 15, 17, 20, 21, 23, 25, 27, 29 days, or longer. Rapid healing of the pleural injuries also suggests that the sealant physically bridges the pleural gap after injury and functions as a scaffold for wound healing.

EXAMPLES

The invention is further described in the following examples, which do not limit the scope of the invention described in the claims.

Example 1

Methods of Making a Pectin-Based Polymer Film

The pectins used in this study were commercially obtained (Cargill, Minneapolis, Minn., USA). The proportion of galacturonic acid residues in the methyl ester form determined the degree of methoxylation. High-methoxyl pectins (HMP) are defined herein as those pectins with a degree of methoxylation greater than 50%; low-methoxyl pectins were defined as less than 50%. Low-methoxyl pectins were also tested as non-amidated, low-methoxyl pectin (LMC) and amidated, low-methoxyl pectin (LMA) variants.

For the 50% HMP pectin-based composition, one gram of HMP was mixed with one gram of CMC. The combination of pectins was mixed with 40 mL deionized water. This mixture was placed in a warm water bath (60° C.) for 4 hours, with gentle stirring every 30 minutes. When the pectin was completely solubilized, the pectin was distributed into 60 mm diameter plates with sufficient volume to cover the entire base of the plate. The plates were then placed in a fume hood at room temperature to cure overnight (approximately 12 hours).

Example 2

Testing of Pectin-Based Polymer Films in a Mouse Model

Methods

The pectin-based polymer films from Example 1 were tested on mouse mesothelial tissues in vitro for bioadhesion studies and in vivo for mouse lung pressure decay studies. Male mice, eight to ten-week old wild type C57BL/6 (Jackson Laboratory, Bar Harbor, Me., USA), were anesthetized prior to euthanasia.

For scanning electron microscopy (SEM), the specimens were fixed by immersion in 2.5% buffered glutaraldehyde. After coating with 20-25 A gold in an argon atmosphere, the mesothelial layer was imaged using a Philips XL30 ESEM scanning electron microscope (Philips, Eindhoven, Netherlands) at 15 Key and 21 µA. Stereo pair images were obtained using a tilt angle difference of 6° on a eucentric sample holder using standardized processing.

For transmission electron microscopy (TEM), lungs designated for microscopy were harvested after cannulation of the trachea. The tissue was fixed by instillation of 2.5% buffered glutaraldehyde into the bronchial system followed by the instillation of 50% O.C.T. Tissue-Tek (Fisher Scientific, Schwerte, Germany) in saline. Post-fixation samples of the lung were embedded in Epon (Serva, Heidelberg, Germany); 700 A ultrathin sections were analyzed using a Leo 906 digital transmission electron microscope (Leo, Oberkochen, Germany).

Mesothelial staining was performed with *Lycopersicon esculentum* lectin (LEL). Derived from the common tomato, the lectin bound oligosaccharides of N-acetyl-D-glucosamine specificity. The biotinylated lectin was obtained from Vector Laboratories (Burlingame, Calif., USA). For lectin histochemistry, cryostat sections were obtained from lung, liver, bowel and heart specimens, embedded in O.C.T. compound, and snap frozen. After warming the slide to 21° C., the sections were fixed for 10 minutes (2% paraformaldehyde and PBS at pH 7.43). The slides were washed with buffer (PBS, 5% sheep serum, 0.1% azide, 1 mM MgC'2, 1 mM $CaCl_2$) and blocked with 20% sheep serum in PBS. The slides were treated with LEL lectin followed by avidin-fluorescein (Southern Biotech, Birmingham, Ala., USA) or avidin-fluorescein alone as a control. The slides were incubated for one hour at 21° C., washed 3 times and mounted with DAP1-containing medium (Vector Laboratories. Burlingame, Calif., USA).

For fluorescence microscopy, the tissue sections were imaged with a Nikon Eclipse TE2000 inverted epifluorescence microscope using Nikon objectives of 1 Ox and 20× linear magnification with infinity correction. An X-Cite™ (Exfo, Vanier, QC, Canada) 120 W metal halide light source and a liquid light guide were used to illuminate the tissue samples. The excitation and emission filters (Chroma Technology, Bellows Falls, Vt., USA) were controlled by a MAC5000 controller (Ludl, Hawthorne, N.Y., USA) and MetaMorph® software 7.8 (Molecular Devices, Downington, Pa., USA). The fluorescence microscopy 16-bit fluorescent images were recorded on a C9100-02 camera (Hamamatsu, Japan), digitally recombined and pseudocolored based on recording wavelength. Nuclear staining with DAPI (Vector Laboratories) ethidium (Sigma-Aldrich), and Hoechst 33342 (Sigma) were used to evaluate the monolayer.

Load/displacement measurements were made using an apparatus customized for tissue application. Loads were applied at comparable rates; tissue displacement was digitally recorded and analyzed by MetaMorph® 7.8 morphometry software (Molecular Devices, Downington, Pa., USA). For all three bioadhesion tests, the pectin mixtures provided a rigid interface upon which the tissue adherend was applied. The forces were applied to the various tissues with a Prolene suture (Ethicon, Somerville, N.J., USA) passed through the tissue within 2 mm of the adhesive interface. All three tests were performed with uniaxial load application; all loads were applied to uniform cross-sectional areas of bioadhesion. Adhesion development time was comparable for all specimens; all tests were performed after warming samples to near −37° C. Tensile strength was tested at a 90° load application, peel strength was tested at a 120° angle of separation, and shear resistance tested by forces applied parallel to the adhesive interface.

For enzyme treatment testing, the tissues were treated with three commercially obtained enzymes previously used to treat mesothelium (Sigma-Aldrich, St. Louis, Mo., USA): hyaluronidase cleaved the 1→4 linkages between N-acetyl-D-glucosamine and D-glucuronate; neuraminidase, also called sialidase, cleaved the glycosidic linkages of neuraminic acids; pronase is a mixture of proteases derived from *Streptomyces griseus*. Enzyme solutions and tissues were maintained at 37° C. during either a 5 minute (pronase) or 90-minute incubation (hyaluronidase and neuraminidase). Following enzyme treatment, the tissues were washed with PBS 3 times.

For silver nitrate staining, the pleural mesothelium was washed with a glucose solution (50 mg/ml) for 3 minutes, exposed to 0.4 mg/ml silver nitrate in situ for 30 sec followed by another 3-minute wash with the glucose solution. The tissue was exposed to UV light for 30 seconds. After brief drying with Argon gas, the pleural was mounted and staining was performed as described by Lee et al. (J. Biomech., 41:3274-7, 2008).

Statistical analyses were based on measurements in at least three different specimens. The unpaired Student's t-test for samples of unequal variances was used to calculate statistical significance. The data was expressed as mean±one standard deviation. The significance level for the sample distribution was defined as $p<0.05$.

Results

Mesothelium has a characteristic "flagstone" appearance by scanning electron microscopy (SEM) (FIG. 1A). Transmission electron microscopy demonstrated that free surface of the mesothelium was covered by microvilli (FIG. 1B, bracket); the basal layer was delimited by a discrete basement membrane (FIG. 1B, arrows). The mesothelial glycocalyx was not visible using electron microscopy; however, fluorescent lectin staining demonstrated a prominent glycocalyx expressed on the free surface of the lung, liver, bowel and heart mesothelium (FIG. 1C).

Figures 2A, 2B, 2C:
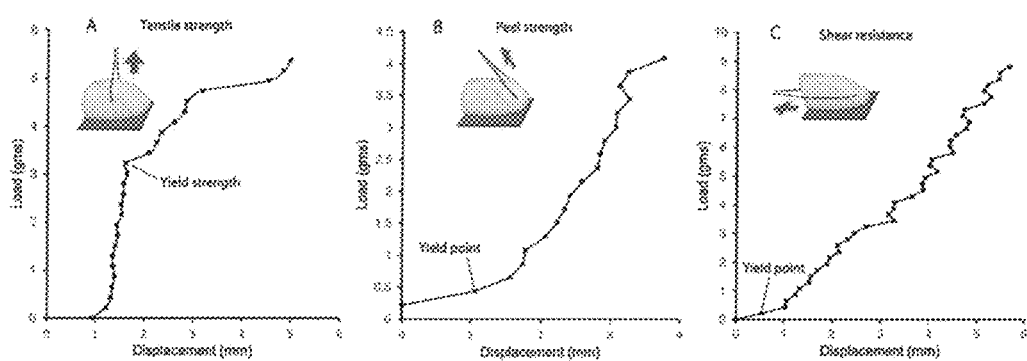
FIGS. 2A to 2C are a series of load/displacement measurement graphs. The adhesion of mesothelium to the pectin-based bioadhesive compositions described herein was assessed by three factors: tensile strength (FIG. 2A), peel strength (FIG. 2B), and shear resistance (FIG. 2C). The tissue was applied, with gentle manual pressure and comparable development time, to the firm pectin-based substratum composed of 50% pectin and 50% carboxymethylcellulose. Loads were applied at a controlled rate to a suture passed through the tissue near the adhesive interface. The lung demonstrated tensile strength (2A) greater than peel strength (2B), or shear resistance (2C). The adhesion of lung to equal weight % pectin and carboxymethylcellulose is shown. Notably, peel and shear forces applied to the lung demonstrated near-interface parenchymal separation (yield point) that facilitated the isolation of the pleural mesothelium.

The bioadhesive pectin and CMC compositions described in Example 1, comprising equal weight percentages of both components, were used to screen for mesothelial adhesion. Uniform and malleable, the lung was used for initial adhesion studies. The lung visceral pleura tissue was applied to the pectin-CMG substratum for a 3-minute development period. The interface was subsequently tested for tensile strength, peel strength (120°) and shear resistance (FIGS. 2A to 2C). The tensile force required to disrupt the pectin-lung interface (yield strength) was more than 6-fold greater than the comparable displacement produced by the peel force and shear force (FIGS. 2A-2C). An interesting observation was the near-interface structural failure of the lung parenchyma when exposed to progressive peel and shear force (yield point, FIGS. 2B, 2C).

Figures 3A, 3B, 3C, 3D, 3E:
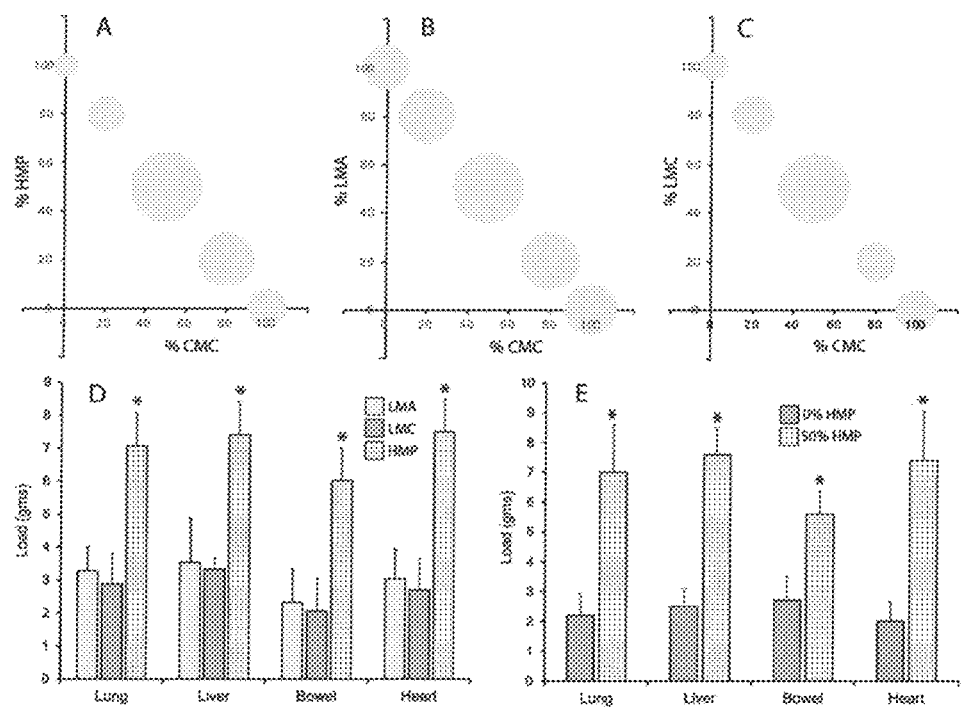
FIGS. 3A to 3E are a series of graphs of the tensile strength of visceral mesothelium adhesion to varied mixtures of pectin and carboxymethylcellulose (CMC).
Figures 4A, 4B, 4C, 4D:
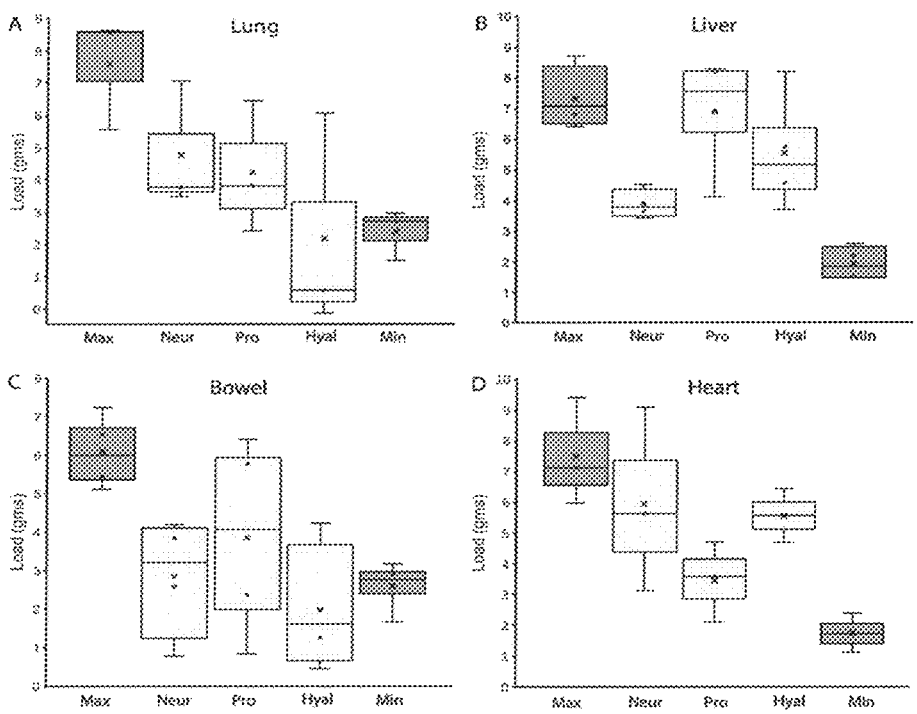
FIGS. 4A to 4D are box plot graphs showing the bioadhesion of visceral mesothelium after pretreatment with glycocalyx-directed enzymes. The lung (A), liver (B), bowel (C), and heart (D) tissue was treated with neuraminidase (Neur), pronase (Pro), or hyaluronidase (Hyal) at established concentrations (Sironi et al., Respir. Physiol. Neurobiol., 188:60-5, 2013). The 50% high-methoxyl pectin (Max) and 0% pectin (Min) provided control comparisons for the enzyme effects on tensile strength. Tensile strength was diminished by all three enzymes; however, significant quantitative variation in enzyme inhibition was noted. Box plots indicate median values and 25th and 75th percentile; whiskers represent variability outside the upper and lower quartiles. Data represents replicate samples of N=3 mice.

To determine the pectin-based compositions that were the most bioadhesive, three types of pectin, low methoxyl (LMC), amidated low-methoxyl (LMA), and high-methoxyl (HMP) pectins, were tested with varying concentrations of CMC. When tested on liver mesothelium, all three pectin formulations demonstrated maximum adhesion with an equal weight ratio (%) with CMC (FIGS. 3A-C). For all four mesothelial tissues, HMP consistently demonstrated greater adhesivity than either LMC or LMA pectin (p<.OS) (FIG. 3D). The quantitative contribution of HMP to mesothelial adhesion was demonstrated when an equal weight % of HMP and CMC (50%) was compared to CMC alone (0%). The equal weight mixture of HMP and CMC demonstrated significantly greater adhesive strength ($p<0.01$) (FIG. 3E).

To test the dependence of pectin bioadhesion on the mesothelial glycocalyx, we treated the mesothelial tissues with hyaluronidase, pronase, and neuraminidase as described generally in Sironi et al. (Respir. Physiol. Neurobiol., 188:60-5, 2013). The enzyme treated mesothelium demonstrated diminished tensile strength of the pectin-based adhesion (FIGS. 4A-4D). The average reduction of pectin adhesion was lung 58±17%, liver 35±27%, bowel 85±29% and heart 37±31%. The variable efficacy of the different enzyme treatments suggested structural differences in the mesothelial glycocalyces of the four tissues. Nevertheless, the new pectin-based compositions were strongly bioadhesive to all mesothelial tissues tested.

Figures 5A, 5B, 5C:
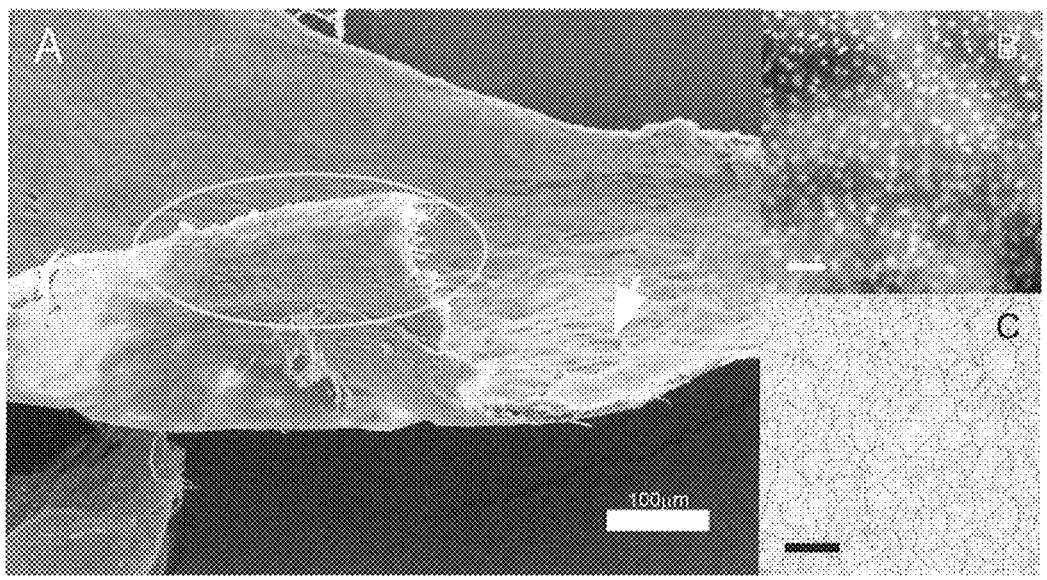
FIGS. 5A to 5C are a series of micrographs illustrating shear and peel force isolation of en face pleural mesothelium. A combination of shear force and peel force applied to the lung-pectin adhesion resulted in the separation of the mesothelium from the subjacent lung.

In testing near-interface separation, we assessed lung adhesion. Peel and shear resistance at the lung/pectin adhesive interface was associated with structural "failure" in the subjacent lung (yield point, FIG. 2B). The parenchymal separation occurred in the subpleural alveoli. Assisted by limited blunt dissection, combined shear and peel forces removed the bulk of the lung parenchyma leaving a 30-50 micron thick layer with an intact basement membrane adherent to the pectin. With hydration, the separated mesothelial layer was "floated off" the pectin adhesive leaving an en face preparation (FIG. 5A). The en face layer was a continuous monolayer (FIG. 5B) with intact tight junctions by silver staining (FIG. 5C).

Discussion

Four features of the bioadhesive interaction between pectin biopolymers and the glycocalyx of visceral mesothelium were tested in this example:

1) An equal weight % mixture of pectin and CMC demonstrated significant tensile strength in adhesion to the lung, liver, bowel, and heart mesothelium.

2) HMP demonstrated greater adhesivity than low-methoxyl or amidated low-methoxyl pectin compounds.

3) Consistent with a mechanism of polysaccharide-dependent adhesion, pectin binding was diminished by enzyme treatment, but the new pectin-based compositions showed strong bioadhesion to all mesothelial tissues tested.

4) Shear force applied to the pectin/lung adhesion resulted in near-interface structural failure—a reproducible observation that facilitated the selective isolation of the mesothelial layer of the lung. We conclude that pectins bind the mesothelial glycocalyx, likely through a mechanism of interpenetration, providing a useful tool in experimental and therapeutic manipulations of the lung, liver, bowel, spleen, and heart mesothelium.

The adhesion measurements performed in this work were a modification of existing adhesion testing methods (Volume 15.06 Adhesives. Annual Book of ASTM Standards. West Conshohocken, Pa.: ASTM International; 2017). In most industrial methods, adhesion is the strength of the bond between the adherend (e.g., tape) and the substratum (application surface). In the present application, the adherend was biological tissue and the substratum was the pectin-based polymer. Unable to usefully distinguish the relative contributions of the tissue, the adhesive bond, and the pectin-based substratum, we empirically defined adhesive strength as the load at which tissue-substratum separation occurred. Tensile strength, peel adhesion and shear resistance simply reflected the direction of the applied load. The validity of this approach was suggested by the reproducible and discriminating measures of pectin-based polymer adhesion to the lung, liver, bowel, and heart. Further, adhesive strength appeared to reflect polysaccharide-dependent adhesion as tensile strength was notably influenced by pectin concentration, pectin chemistry, and enzyme pre-treatment.

The mesothelial binding of the pectin-based bioadhesives described in this example support several useful applications of these compounds in tissue engineering, wound healing, and drug delivery based on their tight binding to the mesothelial glycocalyx. In addition to providing a scaffold for mesothelial regeneration, pectin-based compositions can facilitate the delivery of drugs or growth factors to the mesothelial surface. Additional mesothelial treatment as described herein involve the inhibition of post-treatment serosal adhesions that often lead to bowel obstruction in the peritoneum, impaired lung function in the pleura, and compromised heart function in the pericardium.

In the lung, the shear-induced subpleural structural failure and the reversibility of the pectin-based bioadhesives were unique properties that facilitated the isolation of visceral pleural mesothelium and preserved the en face monolayer relationships that exist in situ. Similar structural failure was not observed in the liver, bowel, and heart. The use of pectin-based adhesion to isolate intact mesothelium represents a significant advance over previous methods.

Example 3

Further Testing of Pectin-Based Polymer Films on Mouse Pleura Methods

The peptide-based compositions used herein were made as described in Example 1. Male mice, eight to ten week old wild type C57BL/6 (Jackson Laboratory, Bar Harbor, Me., USA) were anesthetized prior to euthanasia. The animals were anesthetized with an intraperitoneal injection of Ketamine 100 mg/kg (Fort Dodge Animal Health, Fort Dodge, Iowa) and Xylazine 10 mg/kg (Phoenix Scientific, Inc., St. Joseph, Mo.). Prior to mechanical ventilation, the glottis was directly visualized and intubated with a standard 18 gauge angiocatheter to facilitate forced oscillation measurements (BD Insyte, Sandy, Utah). After intubation, the animal was transferred to a FlexiVent® rodent ventilator (Scireq, Montreal, QC Canada).

The thickness of the pectin-based polymers were measured three times on different preparations with an Ames engineering micrometer (Ames, Waltham, Mass.) gently applied parallel to the sheet surface. Data represents the mean of replicate measurements.

Standard pleural injuries were created with a 25 g needle (Becton Dickinson) with a diameter of 0.51 mm, inserted 1-2 mm into the mouse lung. For comparison, the surface area injury, scaled to the average human lung surface area, would be 2.1 $cm^2$.

Bioadhesion testing was similar to the test used in Example 2 above. Briefly, the pectin-based adhesive and the comparison surgical products provided a rigid interface upon which the pleural adherend was applied. The forces were applied with a 6-0 Prolene® suture (Ethicon) passed through the tissue within 2 mm of the adhesive interface. The test was performed with a controlled rate of uniaxial load applied to a comparable cross-sectional area. Adhesion strength was tested at a 90° load application.

Prior to all measurements, the pressure transducers and ventilator tubing of the FlexiVent® (SciReq, Montreal, QC) were calibrated as described in Gibney et al. (Exp. Lung Res., 38:396-405, 2012). After general anesthesia and intubation, the mice were transferred to the FlexiVent® system (SciReq) for pulmonary mechanics studies. The animals were hyperventilated at a rate of 200/minute and allowed to acclimate to the ventilator for two minutes prior to standardization of the volume history with 3 consecutive positive pressure recruitment maneuvers ("TLC" by SciReq). After recruitment, two maneuvers were performed. First, dynamically determined pressure volume loops (PV-P by SciReq) were created starting from a PEEP of 3 cm $H_2O$ by an 8-second steady inflation ramp to 30 cm $H_2O$ with a 8-second passive deflation. Second, mechanical ventilation was briefly stopped and the animal passively exhaled to functional residual capacity; an 8-second multi-frequency (0.5-19.5 Hz) oscillatory signal (Prime-8 by SciReq) was delivered. Mechanical ventilation was resumed on completion of the Prime-8 maneuver. The pulmonary mechanics were performed prior to and after lung injury as well as following the application of the pectin sealant.

Respiratory system impedance (Zrs) includes the components representing the lung (ZL) and chest wall (Zw) (Hantos et al., J. Appl. Physiol., 73:427-33, 1992). The constant phase model (Hantos et al., J. Appl. Physiol., 72:168-78, 1992) was fit to the input impedance to derive Newtonian resistance (Rn), tissue damping (G), tissue elastance (H), and hysteresivity ($\eta$) as described below:

$$Zrs = Rn + jwI + (G - jH)/\omega\alpha \text{ where } \alpha = (2/\pi)\tan^{-1}(1/\eta)$$
$$\text{and } \eta = G/H$$

A minimum of three measures were taken per animal. Quality control required a minimum coherence of 0.89.

The specimens were fixed for scanning electron microscopy (SEM) by immersion in 2.5% buffered glutaraldehyde. After coating with 20-25 A gold in argon atmosphere, the mesothelial layer was imaged using a Philips XL30 ESEM scanning electron microscope (Philips, Eindhoven, Netherlands) at 15 Key and 21 µA. Stereopair images were obtained using a tilt angle difference of 6° on a eucentric sample holder using standardized computerized control.

The surgical products compared to the pectin-based adhesive sealant were obtained from commercial sources and stored at controlled room temperature. Surgicel® Original, oxidized regenerated cellulose, was obtained from Ethicon (Neuchatel, Switzerland). Seprafilm® Adhesion Barrier, chemically modified sodium hyaluronate/carobxymethylcellulose absorbable adhesion barrier was obtained from Genzyme Biosurgery (Framingham, Mass. USA). TachoSil® fibrin sealant patch was obtained from Baxter Healthcare (Deerfield, Ill., USA). Surgifoam® absorbable gelatin sponge was obtained from Ethicon (Somerville, N.J.). The Prolene® Surgical Mesh was obtained from Ethicon (Somerville, N.J.). Vetbond® Surgical Adhesive was obtained from 3M (St. Paul, Minn.).

Results

Figures 6A, 6B:
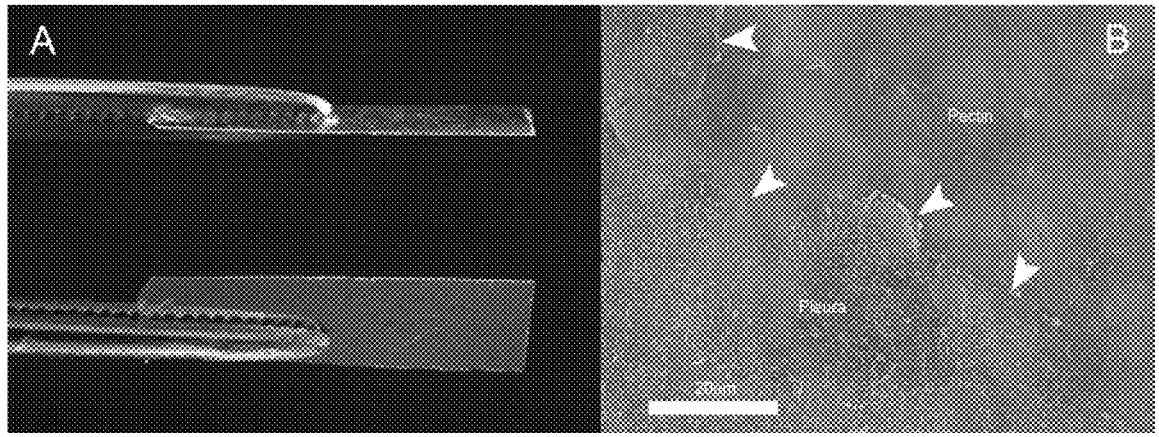
FIG. 6A is a representation of the pectin-based compositions in the form of a thin film. The pectin-based biopolymer was prepared as a 50-50 (wt %) viscous liquid mixture of high methoxyl pectin (HMP) and carboxymethylcellulose (CMC), poured into a mold to form a thin film, and dried overnight into a translucent 50 μm thick sheet (48.3±13 μm).
FIG. 6B is an SEM micrograph showing the pectin-based bipolymer thin film applied to a lung surface with 1-2 minutes of gentle pressure. The image shows the intimate integration of the polymer with the existing pleura. Arrows highlight the edge of the pectin bipolymer covering the mesothelial microvilli.

The HMP and CMC mixture was prepared as a viscous liquid, poured into the desired mold, and allowed to dry overnight. In most experiments, the pectin-based mixture was prepared as a translucent 50 µm thick sheet (48.3±13 µm) (FIG. 6A). With warming, the pectin-based sheet readily conformed to the pleural surface and demonstrated near-maximal adhesion within a 1-2 minute development time. Scanning electron microscopy (SEM) images of the post-application pectin-based polymer created the visual impression that the sheet had "melted" into the mesothelial surface (FIG. 6B). The relative strength of the pectin-based adhesion was demonstrated in comparison to commonly available commercial surgical products used for a variety of surgical applications (FIGS. 7A-7B). The pectin-based polymer demonstrated significantly greater adhesive strength and greater yield strength than the comparison products (p<0.001) (FIGS. 7A-7B).

During general anesthesia and mechanical ventilation, a reproducible pleural injury was created with a 25 g needle inserted 1-2 mm into the visceral pleura. Leaking air and traces of blood were immediately observed after injury. SEM demonstrated a reproducible pleural injury with a consistent absence of a submesothelial matrix (results not shown). To assess the potential function of the pectin-based polymer as an "air tight" sealant, the polymer was applied to the pleural wound. After 1-2 minutes, a lung recruitment maneuver was performed (3 second ramp to 30 cm $H_2O$ pressure). After a single pleural injury, there was a reproducible loss of pressure at 30 cm $H_2O$ and a new plateau pressure at 15 cm $H_2O$ (FIG. 8A). After the pectin-based polymer was applied to the injury and a repeat recruitment maneuver was performed, there was a consistent restoration of the normal plateau pressures (FIG. 8A). To test the effectiveness of the pectin-based sealant in more complex injuries, a "through-and-through" injury (injury×2) of the lung was created with a 25 g needle. During subsequent recruitment maneuvers, there was a loss of plateau pressures similar to the single injury. After sequential applications of the pectin-based sealant (seal×1 and seal×2), there was a progressive restoration of the baseline plateau pressures (FIG. 8B)

A potential limitation of any pleural sealant is lung restriction; that is, the effect of the sealant on limiting lung expansion. To separate the peripheral and central mechanical effects of the sealant, two oversized polymers (25 $mm^2$ and 50 $mm^2$) were applied to the lung surface and compared to no sealant (baseline) and two cyanoacrylate (Vetbond®) controls. After application of the sealant, multi-frequency lung impedance data was fitted to the constant-phase model. As expected, the application of the pectin-based sealant had no effect on central airway resistance (no sealant, Rn=4.75±0.017 cm $H_2O$.s/ml; pectin-based sealant, 50 $mm^2$ Rn=0.484±0.026 cm $H_2O$.s/ml). In contrast, measures of tissue damping (G) demonstrated a slight effect with the larger pectin-based sealant (p>0.05) and a significant effect with both cyanoacrylate (VetBond®) conditions (p<0.01) (See FIG. 9A). Hysteresivity ($\eta$), reflecting the relationship between energy dissipation and energy storage, demonstrated no significant change after the application of the pectin-based polymer (See FIG. 9B).

Since the pectin-based mixture is bioabsorbable, the effects of the applied pectin were studied during the 7-day timeframe typical for pleural healing. Although ethical restrictions precluded a no-treatment control condition, experience with inadvertent lung injuries after murine surgery suggested that untreated air leaks are near-uniformly fatal. Here, application of the pectin-based pleural sealant resulted in 100% survival (N=5). Daily observations of control littermates demonstrated no difference in respiratory rate, respiratory effort, ruffled fur, and activity level. Similarly, there was no detectable change in body weight (pre-injury 26.5±2.4 gms versus 7 days post-injury+sealant 36.6±1.8 gms). Examination of the site of pleural injury 7 days later demonstrated a detectable residual sealant, but no pleural effusion and no pleural adhesions. SEM demonstrated some suggestion of resorption of the sealant, but residual polymer with an appearance consistent with its original application (results not shown). Functional studies of the mice 7 days (POD7) after their original injury demonstrated normal plateau pressures (FIG. 10A) and no detectable air leak (FIG. 10B).

Discussion

Air leaks after pleural injury can have a significant impact on patient care and healthcare costs. Here, we tested the sealant properties of an equal mixture (wt %) of HMP and CMC, for the treatment of pleural injury. We identified four features of the pectin-based sealant. 1) The pectin-based polymer demonstrated a significantly stronger pleural bond than commonly available surgical products. 2) A 1-2 minute development time was sufficient to seal air leaks under positive pressure (30 cm $H_2O$). 3) Despite application of the polymer to 30% of the lung surface area, there was no significant compromise of lung expansion. 4) The sealant was partially reabsorbed, without detectable adhesions or pleural effusions, within 1 week after application. We conclude that the pectin-based polymer is a promising sealant for the treatment of pleural injury.

The pectin-based adhesive polymer demonstrated several additional features characteristics of an ideal sealant. The pectin-based sealant appeared to be safe and nontoxic. Constituted as a 50 μm thick film, the pectin-based sealant was easily prepared and readily applied to the injured pleura. The pectin-based film required only 1-2 minutes of contact time to seal the air leak. Scanning electron microscopy (SEM) suggested that the sealant persisted throughout the typical 7-day healing process without evidence of pulmonary edema or pleural effusion.

The dehydrated pectin-based polymer was relatively inflexible; the polymer was not tacky to touch nor adhesive to non-polysaccharide surfaces. With the warming and gentle hydration associated with pleural application, however, the pectin-based polymer acquired its distinctive properties. The polymer became soft, flexible, and strongly adherent to the pleural surface. The application of a densely adherent polymer to the pleural surface raised the possibility of functional restriction (Loring et al., J. Thorac. Cardiovasc. Surg., 134:204-9, 2007); that is, the polymer might limit lung expansion and diminish parenchymal compliance. Here, we applied the pectin-based polymer to larger surface areas than would be anticipated in clinical use—more than 30% of the lung surface—and studied the consequences using a forced oscillation technique (Pride, Thorax., 47:317-20, 1992). The multi-frequency lung impedance data was fitted to the constant-phase model to discriminate central versus peripheral effects. As expected, the presence or absence of the polymer had no effect on central airway resistance.

Unexpectedly, there was also no significant difference in tissue damping (G) and hysteresivity (ii) before and after the application of the polymer. A potential explanation for this observation is that pectin—depending upon ion concentration, solvent conditions, and degree of cross-linking—can demonstrate significant elasticity. Also, greater viscoelastic properties of interacting polysaccharides (including pectins) have been observed with increased crosslinking and enhanced polysaccharide structure. Based on these observations, it is possible that the pectin film mirrors the endogenous glycocalyx in accommodating the tidal changes in pleural surface area.

The key to the function of the pectin-based sealant is the mesothelial glycocalyx, a polysaccharide coating of the mesothelium of the lung, liver, heart, bowel, and tunica vaginalis. In these experiments, the mesothelial glycocalyx functions as the target substrate for the pectin-based sealant.

Example 4

Testing of Pectin-Based Polymer Films with Human Pleural Tissue

Materials and Methods

The pectin-based compositions used herein were made as described in Example 1. Male mice, eight to ten week old wild type C57BL/6 (Jackson Laboratory, Bar Harbor, Me., USA) were anesthetized prior to euthanasia. The specimens were obtained from a lung region remote to the surgical pathology.

Biotinylated lectins were obtained from commercial sources (lectins from Vector Laboratories (Burlingame, Calif., USA) were: *Maackia amurensis* (MAL-1), *Sambucus nigra* (SNL), *Solanum tuberosum* (STA), and wheat germ agglutinin (WGA)). *Concavalia ensiformis* (ConA) was obtained from Dako (Carpinteria, Calif., USA).

Cryostat sections were obtained from lung specimens perfused with O.C.T. compound and snap frozen. After warming the slide to 27° C., the sections were fixed for 10 minutes (2% paraformaldehyde and PBS at pH 7.43). The slides were washed with buffer (PBS, 5% sheep serum, 0.1% azide, 1 mM $MgCl_2$, 1 mM $CaCl_2$) and blocked with 20% sheep serum in PBS. The slides were treated with the lectin followed by avidin-fluorescein ((Southern Biotech, Birmingham, Ala., USA) or avidin-fluorescein alone control. The slides were incubated for one hour at 27° C., washed 3 times and mounted with DAPI-containing medium (Vector Labs. Burlingame, Calif., USA).

Tissues were treated with a combination of commercially obtained enzymes previously used to treat mesothelium (Sigma-Aldrich, St. Louis, Mo., USA): hyaluronidase cleaving the 1-4 linkages between N-acetyl-D-glucosamine and D-glucuronate; neuraminidase, also called sialidase, cleaving the glycosidic linkages of neuraminic acids; pronase is a mixture of proteases derived from *Streptomyces griseus*. Enzyme solutions and tissues were maintained at 37° C. during a 60-minute incubation. Following enzyme treatment, the tissues were washed with PBS three times.

A simulacrum used for testing the pleural sealants was custom-designed for the FlexiVent® ventilator (See FIG. 12A). The mounting chamber, 1.1 ml in gas volume, was a polypropylene cylinder containing two Mediprene® thermoplastic elastomer mounting gaskets (Hexpol TPE, Sandusky, Ohio, USA). The mounting gaskets provide a pressure resistant seal for pressure-decay testing. The surface area exposed to the test pressure was 0.785 $cm^2$.

Prior to all measurements, the pressure transducers and ventilator tubing of the FlexiVent® (SciReq, Montreal, QC) were calibrated as described in Example 3. Similar to previously described commercial (Extrand et al., Ind. Eng. Chem. Res., 47:1304-9, 2008) and biological leak testing described in Example 2, the chamber was inflated to a target pressure (30 cm $H_2O$), then isolated from the supply pressure. In the standard inflation maneuver, a 3-second ramp to 30 cm $H_2O$ was followed by a 3-second detection phase. The monitored pressure drop reflected the air leak. The rate of pressure decrease with time was used as an index of the leak rate. To extend the pressure limits of the FlexiVent®, the simulacrum was placed in a negative pressure chamber. The 30 cm $H_2O$ positive pressure and the −40 cm $H_2O$ chamber pressure produced a maximal −70 cm $H_2O$ transpleural pressure gradient.

The polymers used in non-biologic testing were obtained from commercial sources with physical properties obtained from Matbase® (www.matbase.com) and the product manufacturer: vulcanized natural latex rubber (latex), Young's modulus 1-2 MPa; acrylonitrile butadiene rubber (nitrile), Young's modulus 2-4 MPa; polyvinyl chloride (vinyl), Young's modulus 10-15 MPa; polyvinylidine chloride (PVCD), Tensile modulus 300-400 mPa. The plastic paraffin film (Parafilm®) was obtained from Bemis NA (Neenah, Wis., USA).

Standard pleural injuries were created with either a 16 g, 19 g, 21 g, 25 g, or 30 g needle (Becton Dickinson, Mountain View, Calif., USA), with an outer diameter of 1.651 mm, 1.067 mm, 0.8192, 0.5144 mm, and 0.3112 mm, respectively. The needle was used to penetrate the mounted pleural membrane.

A bioadhesion test similar to one described in Example 2 was used herein. Briefly, the pectin compound provided an interface upon which the skin, buccal mucosa, or pleura adherend was applied. Adhesion strength reflected the applied force required for interface separation. The test was performed with a controlled rate of uniaxial load applied to tissue. Tensile strength was tested at a 90-degree load application. In all experiments, the results were normalized to a comparable cross-sectional area.

Statistical analysis was based on measurements in at least three different samples. The unpaired Student's t test for samples of unequal variances was used to calculate statistical significance. The data was expressed as mean+one standard deviation. A long-rank (Mantel-Cox) testing was used to determine the significance of the product-limit estimator. The significance level for the sample distribution was typically defined as p<0.05.

Results

To compare the glycocalyx of human and murine pleural mesothelium, we stained the pleural mesothelium of both species with a panel of fluorescent-labeled lectins. The pattern and intensity of the lectin binding was similar (results not shown). To compare the adhesivity of the pectin-based polymer to mouse and human mesothelium, adhesion strength testing (load-distance) was performed as described in Example 2 above. Adhesion of a mixture of 50:50 high-methoxyl pectin (HMP) and carboxymethylcellulose (CMC) to the skin, buccal mucosa, and pleura of the two species was indistinguishable (FIG. 11A). Notably, the adhesion of the pectin mixture to both pleural adherends was significantly greater than the adhesion of the HMP pectin mixture to the skin or mucosa (p<0.001). In contrast to most pressure-sensitive adhesives (not shown), the pectin mixture did not bind to non-biologic commercial materials (FIG. 11B).

To test the effectiveness of pectin-based bioadhesives as "air-tight" sealants of human pleural injuries, we developed a pleural simulacrum that permitted sensitive pressure-decay testing of both human pleura and non-biologic materials. The system was pressurized with a standard inflation maneuver involving a 3 second ramp to a 3 second plateau at 30 cm $H_2O$ (FIG. 12A). Perforation of the pleura with various sized needles resulted in a reproducible pressure-decay; increasingly more perturbed inflation maneuvers were observed with larger holes (FIG. 12C) compared to a baseline (FIG. 12B). In non-biologic testing, the peak pressures reached by the system were related to the size of the pleural injury (results not shown). As expected, elastomeric polymers, such as latex and nitrile were more leak resistant than polymers with minimal elastic properties such as vinyl and PVDC (results not shown).

In human pleural testing, freshly obtained human pleural samples were placed in the simulacrum and a baseline inflation maneuver was performed. The pleura tissue was then perforated with a 19 g or 21 g needle (depending upon tissue thickness) so that a repeat inflation maneuver demonstrated a failure to pressurize the system (e.g., FIG. 12C). After perforation, the sealant was applied and the inflation maneuver was repeated. Four different mixtures of pectin-based sealants were tested (FIGS. 13A-13F); all four mixtures demonstrated sealant efficacy at 30 cm $H_2O$ transpleural pressure. To obtain a greater transpleural pressure gradient and simulate the negative pressure of a therapeutic tube thoracostomy, vacuum was applied to the negative pressure chamber.

Figures 13A, 13B, 13C, 13D, 13E, 13F:
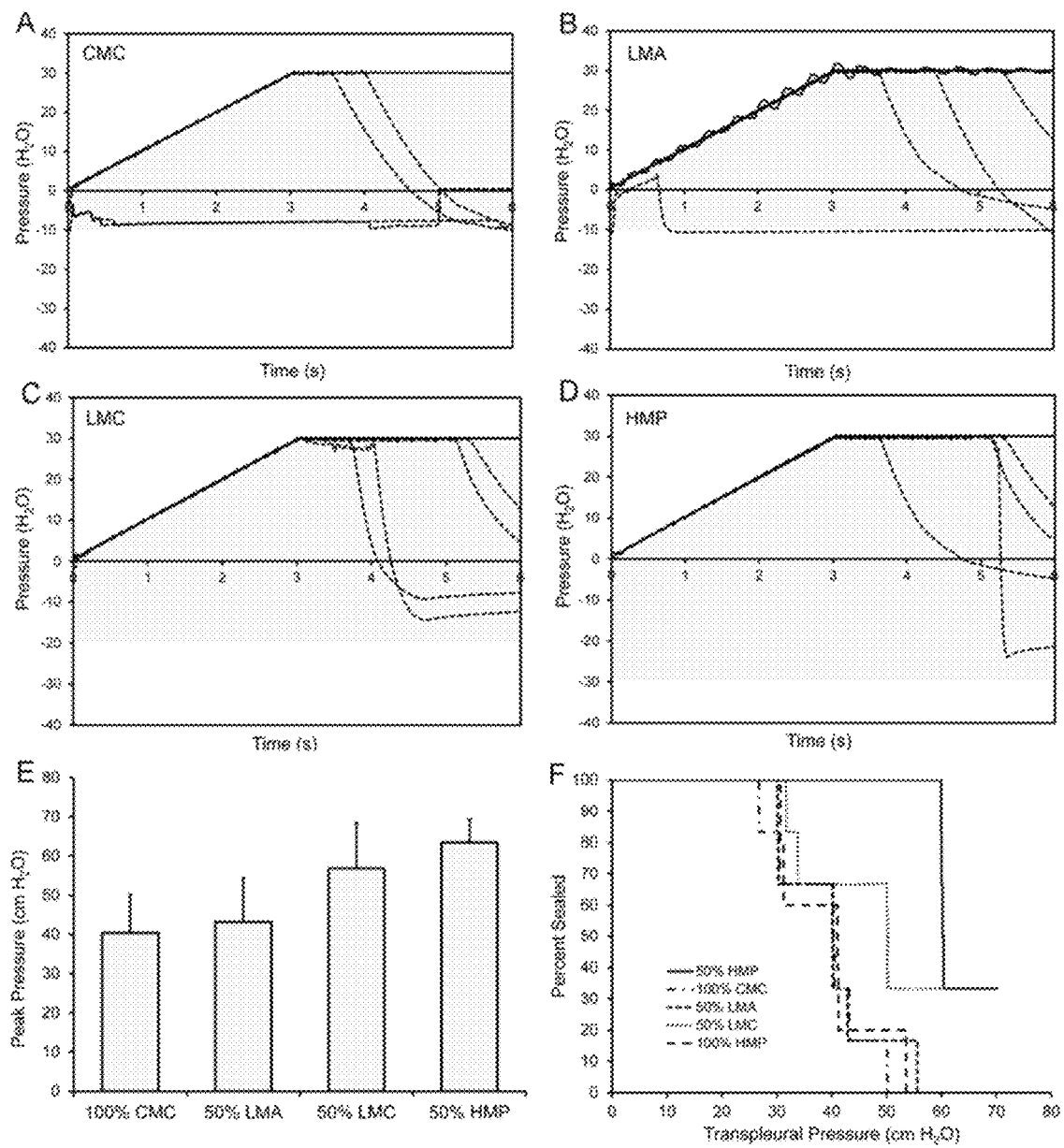
FIGS. 13A to 13F are a series of graphs that show the results of pressure-decay leak testing of human pleura using the simulacrum with carboxymethylcellulose (CMC), high-methoxyl pectin (HMP), low-methoxyl amidated pectin (LMA), and low-methoxyl pectin (LMC).

CMC and LMA demonstrated sealant failures (pressure-decay) at 30 to 40 cm $H_2O$ of transpleural pressure (gray shading shows the level of transpleural pressure). LMC demonstrated no failures less than 50 cm $H_2O$. HMP demonstrated no sealant failures below transpleural pressure of 60 cm $H_2O$ (FIGS. 13A-13D). Although there was some variability with individual pleural tissue samples, sealant strength was reproducibly HMP>LMC>LMA>CMC. HMP mean peak pressures were higher than the other pectins (p<0.05) (FIG. 13E). Similarly, a product-limit estimator was used to determine the transpleural pressure time-to-failure of the pectin-based polymer (FIG. 13F). HMP sealant strength was significantly greater than the other three mixtures (p<0.01).

The mechanism of adhesion was also investigated using the simulacrum and pressure-decay testing. A mechanism of interpenetration requires wetting and swelling of the polymer to permit intimate contact between the sealant and the pleura. Consistent with interpenetration, dehydration of the pleural samples resulted in markedly decreased HMP adhesion (p<0.01). Low temperatures (4° C.), designed to minimize water flux and polymer expansion, also significantly decreased HMP adhesion (p<0.01) (results not shown). Finally, the dependence of HMP adhesion on the glycocalyx was suggested by the effect of the enzyme treatment of the pleura; a mixture of neuraminidase, pronase and hyaluronidase markedly diminished binding of the pectin-based sealant (p<0.01) (results not shown).

Discussion

The similarity between the human and murine glycocalyx shown in Example 2 above suggested the possibility of a comparable sealant function in humans. In this example, we showed the efficacy of structural heteropolysaccharides in sealing human pleura. The striking finding was the adhesion strength between the HMP pectin mixture and the human pleural glycocalyx. In normal human tidal ventilation, pleural pressures vary over a range of 30 cm $H_2O$. Typically, peripheral airway pressures of 15-20 cm $H_2O$ are required to recruit lung volumes from surgery-related or low ventilation-associated atelectasis (Gattinoni et al., N. Engl. J. Med., 354:1775-86, 2006). A person with a strong chest wall can generate pleural pressure gradients over 50 cm $H_2O$ (Butler et al., N. Engl. J. Med., 367:244-7, 2012). In this example, we consistently measured HMP adhesion strength of 60-70 cm $H_2O$. Based on these results, we conclude that structural heteropolysaccharides in general, and high-methoxyl pectins in particular, are promising air-tight sealants of human pleural injuries.

Pectin-based sealants have several additional features that suggest the utility of their clinical application. In contrast to pressure-sensitive adhesives, pectin-based sealants are not "tacky" to the touch, but selectively bind to the pleural mesothelium. The sealant preparation requirements are negligible and binding occurs over a 2-3 minute development time. The mouse studies in Example 2 above demonstrated no pleural adhesions or evidence of toxicity over 7 days. Finally, the presence of pectin-based mixtures in human food and oral medication capsules suggests that the pectin-based sealants will be similarly nontoxic in humans.

The simulacrum was developed to permit the quantitative leak testing of human pleural tissue samples. In addition to sealant testing, the use of the simulacrum provided physiologic insights into pressure-decay observations in the intact lung. The observed pressure plateau suggested inspiratory flow limitation in the peripheral airways. Consistent with this proposed mechanism, injury of the isolated pleura (without airways) did not result in flow limitation.

Finally, the pectin-based polymers have an additional structural feature with therapeutic implications. Upon gelation, the polymers form a corrugated "egg-box" structure. Thus, the pectin-based polymer compositions described herein can incorporate drugs or growth factors to accelerate the healing of pleural and other mesothelial injuries. Together, these results demonstrate that the pectin-based compositions described herein can be used to effectively protect and seal mesothelial tissue wounds and injuries, e.g., to seal "leaks" such as pleural leaks, as well as inhibit post-surgical adhesions.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of covering and sealing a wound in an injured mesothelial tissue, the method comprising:
obtaining a bioadhesive pectin-based polymer film, wherein the film consists of: i) high-methoxyl pectin (HMP) or ii) a complex of HMP and carboxymethylcellulose (CMC) in a ratio from about 10:1 to 1:10 by weight, and iii) water;
applying the film to the wound in the injured mesothelial tissue; and
applying pressure for at least one minute to enable the film to bind to the wound in the injured mesothelial tissue.

2. The method of claim 1, wherein the mesothelial tissue is lung pleura and the method is used to seal an air leak in the lungs.

3. The method of claim 1, wherein the mesothelial tissue is heart mesothelium and the method is used to cover a wound in the heart.

4. The method of claim 1, wherein the mesothelial tissue is bowel mesothelium, and the method is used to seal a surgical site in the bowel.

5. The method of claim 1, wherein the mesothelial tissue is spleen mesothelium and the method is used to repair a ruptured spleen.

6. The method of claim 1, wherein the complex is a 1:1 ratio by weight of HMP and CMC.

7. The method of claim 1, wherein the bioadhesive pectin-based polymer film is a moldable film having a thickness of about 40 to 3000 microns.

8. The method of claim 1, wherein the bioadhesive pectin-based polymer film biodegrades within about seven days.

9. A method of covering and sealing a wound in an injured mesothelial tissue, the method comprising:
obtaining a bioadhesive pectin-based polymer film comprising a complex of high-methoxyl pectin (HMP) and carboxymethylcellulose (CMC) in a ratio of 1:1 by weight;
applying the film to the wound in the injured mesothelial tissue; and
applying pressure for at least one minute to enable the film to bind to the wound in the injured mesothelial tissue.

* * * * *

UNITED STATES PATENT AND TRADEMARK OFFICE
CERTIFICATE OF CORRECTION

| | |
|---|---|
| PATENT NO. | : 10,912,858 B2 |
| APPLICATION NO. | : 15/967071 |
| DATED | : February 9, 2021 |
| INVENTOR(S) | : Steven James Mentzer et al. |

It is certified that error appears in the above-identified patent and that said Letters Patent is hereby corrected as shown below:

In the Specification

Column 1, Line 12, insert --STATEMENT OF FEDERALLY SPONSORED RESEARCH
This invention was made with government support under Grant Nos. HL007734, CA009535, HL134229, ES000002, and HL094567 awarded by the National Institutes of Health. The government has certain rights in the invention.--

Signed and Sealed this
Sixteenth Day of May, 2023

Katherine Kelly Vidal
*Director of the United States Patent and Trademark Office*